US009771395B2

(12) United States Patent
Koday et al.

(10) Patent No.: US 9,771,395 B2
(45) Date of Patent: Sep. 26, 2017

(54) ENHANCED INFLUENZA HEMAGGLUTININ BINDERS

(71) Applicant: UNIVERSITY OF WASHINGTON, Seattle, WA (US)

(72) Inventors: Merika Treants Koday, Seattle, WA (US); Deborah L. Fuller, Seattle, WA (US); Aaron Chevalier, Seattle, WA (US); Jorgen Nelson, Seattle, WA (US); David Baker, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/120,071

(22) PCT Filed: Mar. 20, 2015

(86) PCT No.: PCT/US2015/021780
§ 371 (c)(1),
(2) Date: Aug. 18, 2016

(87) PCT Pub. No.: WO2015/143339
PCT Pub. Date: Sep. 24, 2015

(65) Prior Publication Data
US 2017/0073375 A1    Mar. 16, 2017

Related U.S. Application Data

(60) Provisional application No. 61/968,874, filed on Mar. 21, 2014, provisional application No. 62/028,139, filed on Jul. 23, 2014.

(51) Int. Cl.
*A61K 38/00*    (2006.01)
*C07K 14/00*    (2006.01)
*G01N 33/569*    (2006.01)
*A61K 9/00*    (2006.01)

(52) U.S. Cl.
CPC ....... *C07K 14/00* (2013.01); *G01N 33/56983* (2013.01); *A61K 9/0043* (2013.01); *A61K 38/00* (2013.01); *G01N 2333/11* (2013.01); *G01N 2500/04* (2013.01)

(58) Field of Classification Search
None
See application file for complete search history.

(56) References Cited

U.S. PATENT DOCUMENTS

| 8,470,327 | B2 | 6/2013 | Throsby et al. |
| 8,540,995 | B2 | 9/2013 | Mookkan et al. |
| 8,569,255 | B2 | 10/2013 | Wong |
| 9,181,300 | B2 | 11/2015 | Baker et al. |
| 9,388,217 | B2 | 7/2016 | Baker et al. |
| 2009/0191233 | A1 | 7/2009 | Bonnet et al. |

FOREIGN PATENT DOCUMENTS

| EP | 2003198 A2 | 12/2008 |
| EP | 2327714 A1 | 6/2011 |
| WO | 0059932 | 3/2000 |
| WO | 2005037187 | 4/2005 |
| WO | 2012/018907 A2 | 2/2012 |
| WO | 2012018907 A2 | 2/2012 |
| WO | 2013082531 | 6/2013 |
| WO | 2013121442 | 8/2013 |
| WO | 2013/138259 A2 | 9/2013 |
| WO | 2014152946 A2 | 9/2014 |

OTHER PUBLICATIONS

International Search Report and Written Opinion for PCT/US2015/021780, dated Sep. 30, 2015.
Whitehead, et al., "Optimization of affinity, specificity and function of designed influenza inhibitors using deep sequencing," Nature Biotechnology, 38(6): 543-548, Jun. 2012.
Whitehead, et al., "Supplementary Information for Optimization of affinity, specificity and function of designed influenza inhibitors using next generation sequencing," Nature Biotechnolog,y May 2012, pp. 1-39.
Ofran, Y. and Rost, B. (Jul. 2007) "Protein-protein interaction hotspots carved into sequences," PLoS Comput Biol, 3(7):e119.
Pal, G. et al. (Aug. 2006) "Comprehensive and quantitative mapping of energy landscapes for protein-protein interactions by rapid combinatorial scanning," J Biol Chem, 281(31):22378-85.
Patwardhan, RP et al. (Dec. 2009) "High-resolution analysis of DNA regulatory elements by synthetic saturation mutagenesis," Nat Biotechnol, 27(12):1173-1175.
Pierce, B. and Weng, Z. (Jun. 2007) "ZRANK: reranking protein docking predictions with an optimized energy function," Proteins, 67(4):1078-1086.
Pitt, JN and Ferre-D'Amare, AR (Oct. 2010) "Rapid construction of empirical RNA fitness landscapes," Science, 330 (6002):376-379.
Richards, FM (1977) "Areas, Volumes, Packing, and Protein Structure," Annu Rev Biophys Bio, 6:151-176—retrieved May 2015.
Richardson, JS et al. (Nov. 1992) "Looking at proteins: representations, folding, packing, and design," Biophys. J., 63 (5):1185-1209.
Rittinger, K. et al. (Aug. 1997) "Crystal structure of a small G protein in complex with the GTPase-activating protein rhoGAP," Nature, 388(6643):693-7.
Rittinger, K. et al. (Oct. 1997) "Structure at 1.65 A of RhoA and its GTPase-activating protein in complex with a transition-state analogue," Nature, 389(6652):758-62.
Rohl, CA et al. (2004) "Protein structure prediction using Rosetta," Methods Enzymol, 383:66-93—retrieved May 2015.
Schreiber, G. and Fersht, AR (Apr. 1995) "Energetics of protein-protein interactions: analysis of the barnase-barstar interface by single mutations and double mutant cycles," J Mol Biol, 248(2):478-486.

(Continued)

*Primary Examiner* — Jeanette Lieb
(74) *Attorney, Agent, or Firm* — McDonnell Boehnen Hulbert & Berghoff LLP

(57) ABSTRACT

Designed polypeptides having the amino acid sequence of SEQ ID NQ: 1 are described that bind with high affinity and selectivity to the influenza hemagglutinin protein, and which can be used for treating and/or limiting an influenza infection, as well as diagnosing an influenza infection and identifying candidate compounds for treating an influenza infection.

27 Claims, 8 Drawing Sheets

(56) References Cited

OTHER PUBLICATIONS

Schreiber, G. and Fersht, AR (May 1993) "Interaction of barnase with its polypeptide inhibitor barstar studied by protein engineering," Biochemistry, 32(19):5145-5150.
Schreiber, G. and Fersht, AR (May 1996) "Rapid, electrostatically assisted association of proteins," Nat Struct Biol, 3(5):427-31.
Schreiber, G. et al. (Jul. 1997) "The role of Glu73 of barnase in catalylsis and the binding of barstar," J Mol Biol, 270(1):111-122.
Shriver et al. (Aug. 2009) "Context-specific target definition in influenza a virus hemagglutinin-glycan receptor interactions," Chemistry & Biology, 16(8):803-14.
Shultzaberger, RK et al. (Jul. 2010) "The fitness landscapes of cis-acting binding sites in different promoter and environmental contexts," PLoS genetics, 6(7.
Sitkoff, D. et al. (Feb. 1994) "Accurate Calculation of Hydration Free-Energies Using Macroscopic Solvent Models," J Phys Chem, 98(7):1978-1988.
Sitkoff, D. et al. (Feb. 1996) "Calculation of alkane to water solvation free energies using continuum solvent models," J Phys Chem, 100(7):2744-2752.
Smee, DF et al. (Mar. 2001) "Cyclopentane neuraminidase inhibitors with potent in vitro anti-influenza virus activities," Antimicrob Agents Chemother, 45(3):743-748.
Stanfield, RL et al. (Sep. 2004) "Crystal structure of a shark single-domain antibody V region in complex with lysozyme," Science, 305(5691):1770-3.
Stebbins, CE and Galán, JE (Dec. 2000) "Modulation of host signaling by a bacterial mimic: structure of the *Salmonella effector* SptP bound to Rac1," Molecular Cell, 6(6):1449-1460.
Stevenson, CE et al. (Dec. 2006) "Crystal structure of the MYB domain of the RAD transcription factor from Antirrhinum majus," Proteins: Structure, Function, and Bioinformatics, 65(4):1041-5.
Wallis, R. et al. (Oct. 1995) "Protein-protein interactions in colicin E9 DNase-immunity protein complexes. 1. Diffusion—controlled association and femtomolar binding for the cognate complex," Biochemistry, 34(42):13743-50.
Weiss, MS and Hilgenfeld, R. (Apr. 1997) "On the use of the merging R factor as a quality indicator for X-ray data," J Appl Crystallogr, 30(Pt. 2):203-205.
Wu, X. et al. (Sep. 2011) "Focused evolution of HIV-1 neutralizing antibodies revealed by structures and deep sequencing," Science, 333(6049):1593-1602.
Zahnd, C. et al. (Apr. 2004) "Directed in vitro evolution and crystallographic analysis of a peptide-binding single chain antibody fragment (scFv) with low picomolar affinity," Journal of Biological Chemistry, 279(18)18870-7.
Zanghellini, A. et al. (Dec. 2006) "New algorithms and an in silico benchmark for computational enzyme design," Protein Sci, 15(12):2785-94.
Stebbins, et al. "Structural mimicry in bacterial virulence," Nature, 412:701-705, Aug. 2001.
Sharabi, O. et al. (May 2011) "Triathlon for energy functions: who is the winner for design of protein-protein interactions?" Proteins, 79(5):1487-1498.
Balish, et al. "Influenza: propagation, Quantification, and Storage," Current Protocols in Microbiology, May 2013, Supplement 29, 15G.1.-15.G.1.24.
ABW98089 from NCBI GenBank, p. 1, from PNAS 2007.
Araya, et al., "Deep mutational scanning: assessing protein function on a massive scale," Trends Biotechnol, vol. 29, No. 9, pp. 435-442, 2011.
Araya, et al., "A fundamental protein property, thermodynamic stability, revealed solely from large-scale measurements of protein function," Proceedings of the National Academy of Sciences USA, vol. 109, No. 42, pp. 16858-16863, 2012.
Balakrishnan, et al., "Learning generative models for protein fold families," Proteins, vol. 79, No. 4, pp. 1061-1078, 2011.
Beck, et al., "Strategies and challenges for the next generation of therapeutic antibodies," Nature Reviews Immunology, vol. 10, No. 5, pp. 345-352, 2010.
Benatuil, et al., "An improved yeast transformation method for the generation of very large human antibody libraries," Protein Eng Des Sel, vol. 23, No. 4, pp. 155-159, 2010.
Ben-Shimon, A. and Eisenstein, M. (Sep. 2010) "Computational mapping of anchoring spots on protein surfaces," J. Mol. Biol., 402(1):259-277.
Bershtein, et al., Robustness-epistasis link shapes the fitness landscape of a randomly drifting protein, Nature, vol. 444, No. 7121, pp. 929-932, 2006.
Binz, et al., "Engineered proteins as specific binding reagents," Curr. Opin. Biotechnol., vol. 16, No. 4, pp. 459-469, 2005.
Binz, et al., "High-affinity binders selected from designed ankyrin repeat protein libraries," Nat. Biotechnol., vol. 22, No. 5, pp. 575-582, 2004.
Binz, et al., "Engineering novel binding proteins from nonimmunoglobulin domains," Nat Biotechnol, vol. 23, vol. 10, pp. 1257-1268, 2005.
Binz, et al., "Designing repeat proteins: well-expressed, soluble and stable proteins from combinatorial libraries of consensus ankyrin repeat proteins," J. Mol. Bioi., vol. 332, No. 2, pp. 489-503, 2003.
Bogan, et al., "Anatomy of hot spots in protein interfaces," J Mol Bio1, vol. 280, No. 1, pp. 1-9, 1998.
Boumazos, et al., "Broadly neutralizing anti-HIV-1 antibodies require Fe effector functions for in vivo activity," Cell, vol. 158, No. 6, pp. 1243-1253, 2014.
Bowie, et al., "A method to identify protein sequences that fold into a known three-dimensional structure," Science, vol. 253, No. 5016, pp. 164-170, 1991.
Bowie, et al., "Deciphering the message in protein sequences: tolerance to amino acid substitutions," Science, vol. 247, No. 4948, pp. 1306-1310, 1990.
Braisled, et al.,"Minimizing a binding domain from protein A," Proc Nail Acad Sci USA, vol. 93, No. 12, pp. 5688-5692, 1996.
Buckle, et al., "Protein-protein recognition: crystal structural analysis of a bamase-barstar complex at 2.0-A resolution," Biochemistry, vol. 33, No. 30, pp. 8878-8889, 1994.
Castro, et al., "Alanine point-mutations in the reactive region of bovine pancreatic trypsin inhibitor: effects on the kinetics and thermodynamics of binding to bela-trypsin and alpha-chymotrypsin," Biochemistry, vol. 35, No. 35, pp. 11435-11446, 1996.
CDC "Inftuenza Antiviral Drug Resistance," available online at: http://www.cdc.gov/ftu/aboul/qa/antiviralresistance.htm, 2015.
Chao, et al., "Isolating and engineering human antibodies using yeast surface display," Nature Protocols, vol. 1, pp. 755-768, 2006.
Chao, "Fine epitope mapping of anti-epidermal growth factor receptor antibodies through random mutagenesis and yeast surface display," J Mol Bioi, vol. 342, No. 2, pp. 539-550, 2004.
Chen, "ZDOCK: an initial-stage protein-docking algorithm," Proteins, vol. 52, No. 1, pp. 80-87, 2003.
Choi, et al., "A structural bioinformatics approach for identifying proteins predisposed to bind linear epitopes on pre-selected target proteins," Protein Engineering, Design & Selection, vol. 26, No. 4,pp. 283-289, 2013.
Clackson, et al., "Structural and functional analysis of the 1:1 growth hormone: receptor complex reveals the molecular basis for receptor affinity," J Mol Bioi, vol. 277, No. 5, pp. 1111-1128., 1998.
Connaris, et al., "Prevention of inftuenza by targeting host receptors using engineered proteins," Proceedings of the National Academy of Sciences, vol. 111, No. 17, pp. 6401-6406, 2014.
Corti, et al., "A Neutralizing Antibody Selected from Plasma Cells That Binds to Group 1 and Group 2 Influenza A Hemagglutinins," Science, vol. 333, No. 6044, pp. 850-856, 2011.
Cunningham, et al., "High-resolution epitope mapping of hGH-receptor interactions by alanine-scanning mutagenesis," Science, vol. 244, No. 4908, pp. 1081-1085, 1989.
Dauter, "Data-collection strategies," Acta Crystallogr D Bioi Crystallogr, vol. 55, No. PI. 10, pp. 1703-1717, 1999.

(56) References Cited

OTHER PUBLICATIONS

De Clercq, "Antiviral agents active against influenza A viruses," Nature Reviews Drug Discovery, vol. 5, No. 12, pp. 1015-1025, 2006.

Delano, WL (2002) "The PyMol molecular graphics systems," Delano Scientific, San Carlos, CA, USA. http://www.pymol.org—retrieved May 2015.

Dilillo, et al., "Broadly neutralizing hemagglutinin stalk-specific antibodies require FcγR interactions for protection against influenza virus in vivo," Nature Medicine, 20(2):143-151, 2014.

Dutta, et al., "Determinants of BH3 binding specificity for Mcl-1 versus Bcl-xl," J Mol Bioi, vol. 398, No. 5, pp. 747-762, 2010.

Efron, et al., "Least angle regression," Ann Stat, vol. 32, No. 2, pp. 407-499 retrieved May 2015.

Ekiert, et al., "Broadly neutralizing antibodies against influenza virus and prospects for universal therapies," Current Opinion in Virology, vol. 2, No. 2, pp. 134-141, 2012.

Falcone, et al., "Influenza virus A(H1N1)pdm09 hemagglutinin polymorphism and associated disease in southern Germany during the 2010/11 influenza season," Archives of Virology, vol. 158, No. 6, pp. 1297-1303, 2013.

Fleishman, et al., "Computational Design of Proteins Targeting the Conserved Stem Region of Influenza Hemagglutinin," Science, vol. 332, No. 6031, pp. 816-821, 2011.

Fleishman, et al., "RosettaScripls: A Scripting Language Interface to the Rosetta Macromolecular Modeling Suite," PLoS One, vol. 6(6):e20161, 2011.

Fleishman, et al., "Restricted sidechain plasticity in the structures of native proteins and complexes," Protein Science, vol. 20, No. 4, pp. 753-757, 2011.

Fleishman, "Hotspot-centric de novo design of protein binders," Journal of Molecular Biology, vol. 413, No. 5, pp. 1047-1062, 2011.

Fowler, et al., "High-resolution mapping of protein sequence-function relationships," Nat Methods, vol. 7, No. 9, pp. 741-746, 2010.

Friesen, et al.,"A common solution to group 2 influenza virus neutralization," Proceedings of the National Academy of Sciences USA, vol. 111, No. 1, pp. 445-450, 2014.

Gibson, et al., "Enzymatic assembly of DNA molecules up to several hundred kilobases," Nature Methods, vol. 6, No. 5, pp. 343-345, 2009.

Girard, et al., "The 2009 A (H1N1) influenza virus pandemic: A review," Vaccine, vol. 28, No. 31, pp. 4895-4902, 2010.

Grigoryan, et al., "Design of protein-interaction specificity gives selective bZIP-binding peplides," Nature, vol. 458, No. 7240, pp. 859-864, 2009.

Guharoy, "Conservation and relative importance of residues across protein-protein interfaces," Proc. Nail. Acad. Sci. USA, vol. 102, No. 43, pp. 15447-15452, 2005.

Hackel, et al., "Picomolar affinity fibronectin domains engineered utilizing loop length diversity, recursive mutagenesis, and loop shuffling," Journal of Molecular Biology, vol. 381, No. 5, pp. 1238-1252, 2008.

Havranek, et al., "Automated design of specificity in molecular recognition," Nat. Struct. Bioi., vol. 10, No. 1, pp. 45-52, 2003.

Hietpas, et al., "Experimental illumination of a fitness landscape," Proc Nail Acad Sci USA, vol. 108, No. 19, pp. 7896-7901, 2011.

Hoover, et al., "DNAWorks: an automated method for designing oligonucleotides for PCR-based gene synthesis," Nucleic Acids Research, vol. 30, No. 10, e43, 2002.

Hu, et al., "Conservation of polar residues as hot spots at protein interfaces," Proteins, vol. 39, No. 4, pp. 331-342, 2000.

Huang, et al., "The conserved asparagine in the HNH motif serves an important structural role in metal finger endonucleases," Journal of Molecular Biology, vol. 368, No. 3, pp. 812-821, 2007.

Ichinohe, et al., "Inflammasome recognition of influenza virus is essential for adaptive immune responses," Journal of Experimental Medicine, vol. 206, No. 1, pp. 79-87, 2009.

Ishikawa, et al., "Development of functional human blood and immune systems in NOD/SCID/IL2 receptor {gamma} chain-(null)mice," Blood, vol. 106, No. 5, pp. 1565-1573, 2005.

Ivachtchenko et al. "Novel oral anti-influenza prodrug candidate AV5075S," Journal of Antimicrobial Chemotherafcpy, vol. 69, No. 5, pp. 1311-1324, 2014.

Koyama, et al., "Differential role of TLR- and RLR-signaling in the immune responses to influenza A virus infection and vaccination," Journal of Immunology, vol. 179, No. 7, pp. 4711-4720, 2007.

Krammer, et al., "Influenza virus hemagglutinin stalk-based antibodies and vaccines," Current Opinion in Virology, Voll 3, No. 5, pp. 521-530, 2013.

Kunkel, "Rapid and efficient site-specific mutagenesis without phenotypic selection," Proceedings of the National Academy of Sciences USA, vol. 82, No. 2, pp. 488-492, 1985.

Lambert, et al., "Influenza vaccines for the future," New England Journal of Medicine, vol. 363, No. 21, pp. 2036-2044, 2010.

Lander, et al., "Appion: an integrated, database-driven pipeline to facilitate EM image processing," Journal of Structural Biology, vol. 166, No. 1, pp. 95-1, 2009.

Ludtke, et al., "EMAN: semiautomated software for high-resolution single-particle reconstructions," Journal of Structural Biology, vol. 128, No. 1, pp. 82-97, 1999.

McCullers, "The co-pathogenesis of influenza viruses with bacteria in the lung," Nature Reviews Microbiology, vol. 12, No. 4, pp. 252-262, 2014.

Ohbo, et al., "Modulation of hematopoiesis in mice with a truncated mutant of the interleukin-2 receptor gamma chain," Blood, vol. 87, No. 3, pp. 956-967, 1996.

Patrick, et al., "User-friendly algorithms for estimating completeness and diversity in randomized protein-encoding libraries," Protein Engineering, vol. 16, No. 6, pp. 451-457, 2003.

Seo, et al., "MyD88 signaling is indispensable for primary influenza A virus infection but dispensable for secondary infection," Journal of Virology, vol. 84, No. 24, pp. 12713-12722, 2010.

Shrestha, et al., "Identifying the Interaction Between Influenza and Pneumococcal Pneumonia Using Incidence Data," Science Translational Medicine, vol. 5, No. 191, 191ra184, 2013.

Sorzano, et al., "A clustering approach to multireference alignment of single-particle projections in electron microscopy," Journal of Structural Biology, vol. 171, No. 2, pp. 197-206, 2010.

Studier, "Protein production by auto-induction in high density shaking cultures," Protein Expression & Purification, vol. 41, No. 1, pp. 207-234, 2005.

Suloway, et al., "Automated molecular microscopy: the new Leginon system," Journal of Structural Biology, vol. 151, No. 1, pp. 41-60, 2005.

Tanaka et al., "The effect of intravenous peramivir, compared with oral oseltamivir, on the outcome of post-influenza pneumococcal pneumonia in mice," Antiviral Therapy, vol. 20, No. 1, pp. 11-19, 2014.

Tang, et al., "EMAN2: an extensible image processing suite for electron microscopy," Journal of Structural Biology, vol. 157, No. 1, pp. 38-46, 2007.

Tharakaraman, et al. "Broadly neutralizing influenza hemagglutinin stem-specific antibody CR8020 targets residues that are prone to escape due to host selection pressure," Cell Host & Microbe, vol. 15, No. 5, pp. 644-651, 2014.

Voss et al., "DoG Picker and TiltPicker: software tools to facilitate particle selection in single particle electron microscopy," Journal of Structural Biology, vol. 166, No. 2, pp. 205-213, 2009.

Webster, et al., "Evolution and ecology of influenza A viruses," Microbiological Reviews, vol. 56, No. 1, pp. 152-179, 1992.

Whitehead, et al., "Optimization of affinity, specificity and function of designed influenza inhibitors using deep sequencing," Nature Biotechnology, vol. 30, No. 6, pp. 543-548, 2012.

Humphris, EL and Kortemme, T. (Dec. 2008) "Prediction of protein-protein interface sequence diversity using flexible backbone computational protein design," Structure, 16(12):1777-88.

Hwang, H. et al. (Nov. 2008) "Protein-protein docking benchmark version 3.0," Proteins, 73(3):705-709.

(56) References Cited

OTHER PUBLICATIONS

Jin, L. and Wells, JA (Dec. 1994) "Dissecting the energetics of an antibody-antigen interface by alanine shaving and molecular grafting," Protein Sci, 3(12):2351-7.

Joachimiak, A. (Oct. 2009) "High-throughput crystallography for structural genomics," Curr Opin Struct Biol, 19(5):573-84.

Joughin, BA et al. (May 2005) "Action-at-a-distance interactions enhance protein binding affinity," Protein Sci, 14(5):1363-1369.

Kashyap, AK et al. (Apr. 2008) "Combinatorial antibody libraries from survivors of the Turkish H5N1 avian influenza outbreak reveal virus neutralization strategies," Proceedings of the National Academy of Sciences USA, 105(16):5986-91.

Keeble, AH et al. (Mar. 2006) "Calorimetric dissection of colicin DNase—immunity protein complex specificity," Biochemistry, 45(10)3243-3254.

Kellogg, EH et al. (Mar. 2011) "Role of conformational sampling in computing mutation-induced changes in protein structure and stability," Proteins, 79(3):830-838.

Koide, A. and Koide, S. (2007) "Monobodies: antibody mimics based on the scaffold of the fibronectin type III domain," Methods Mol Biol, 352:95-109—retrieved May 2015.

Kortemme, T. et al. (Feb. 2004) "Computational alanine scanning of protein-protein interfaces," Sci STKE, 2004(219):pl2.

Kruger, DM and Gohlke, H. (Jul. 2010) "DrugScorePPI webserver: fast and accurate in silico alanine scanning for scoring protein-protein interactions," Nucleic Acids Res., 38(Web Server Issue):W480-W486.

Kuhlmann, UC et al. (Sep. 2000) "Specificity in protein-protein interactions: the structural basis for dual recognition in endonuclease colicin-immunity protein complexes," J Mol Biol, 301(5):1163-78.

Leaver-Fay, A. et al. (2011) "ROSETTA3: an object-oriented software suite for the simulation and design of macromolecules," Methods Enzymol, 487:545-574—retrieved May 2015.

Levin, KB et al. (Oct. 2009) "Following evolutionary paths to protein-protein interactions with high affinity and selectivity," Nature Structure and Molecular Biology, 16(10):1049-1055.

Idusogie, EE et al. (Apr. 2000) "Mapping of the C1q binding site on rituxan, a chimeric antibody with a human IgG1 Fc," J Immunol, 164(8):4178-84.

Ma, B. et al. (May 2003) "Protein-protein interactions: structurally conserved residues distinguish between binding sites and exposed protein surfaces," Proc. Natl. Acad. Sci. USA, 100(10):5772-5777.

Mandell, DJ et al. (Aug. 2009) "Sub-angstrom accuracy in protein loop reconstruction by robotics-inspired conformational sampling," Nat Methods, 6(8):551-2.

Marshall, SA et al. (May 2005) "One- and two-body decomposable Poisson-Boltzmann methods for protein design calculations," Protein Sci, 14(5):1293-1304.

Moore, GE (Jun. 1995) "Lithography and the future of Moore's law," Proc. SPIE 2438, Advances in Resist Technology and Processing XII.

Moreffi et al. (Nov. 2013) "Community-wide evaluation of methods for predicting the effect of mutations on protein-protein interactions," Proteins: Structure, Function, and Bioinformatics, 81(11):1980-7.

Murphy, PM et al. (Jun. 2009) "Alteration of enzyme specificity by computational loop remodeling and design," Proceedings of the National Academy of Sciences USA, 106(23):9215-9220.

Nassar, N. et al. (Dec. 1998) "Structures of Cdc42 bound to the active and catalytically compromised forms of Cdc42GAP," Nature Structural Biology, 5(12):1047-1052.

Nguyen, JT et al. (Feb. 2010) "Triple combination of amantadine, ribavirin, and oseltamivir is highly active and synergistic against drug resistant influenza strains in vitro," PLoS One, 5(2):e9332.

Nguyen, JT et al. (Oct. 2009) "Triple combination of oseltamivir, amantadine, and ribavirin displays synergistic activity against multiple influenza virus strains in vitro," Antimicrob Agents Chemother, 53(10):4115-4126.

O'Keefe et al. (Aug. 2003) "Potent anti-influenza activity of cyanovirin-N and interactions with viral hemagglutinin," Antimicrobial Agents and Chemotherapy, 47(8):2518-25.

a  20A filter of 3R2X
b  PR8 + HB36.6
c  PR8+HB36.6 (surface)
   HA (blue)
   HB36.6 (cyan)

d

| $k_D$ (nM) | HB36.5 | HB36.6 |
|---|---|---|
| A/South Carolina/1918 H1 | 1.5 | 1.5 |
| A/California/2009 H1 | 17.4 | 3.1 |
| A/Adachi/1957 H2 | 711.9 | 18.5 |
| A/Vietnam/2004 H5 | 224.8 | 23.5 |
| A/Wisconsin/1966 H9 | 82.8 | 13.2 |
| A/Alberta/1976 H12 | 634 | 496 | e

| $EC_{50}$ (µg/ml) | HB36.6 | Ribavirin |
|---|---|---|
| A/Puerto Rico/1934 (H1N1) | 0.58 | ND |
| A/New Caledonia/1999 (H1N1) | 1.26 | ND |
| A/California/2009 (H1N1) | 0.18 | 15 |
| A/Hong Kong/2003 (H5N1) | 12 | 16 |
| A/Duck/MN/1981 (H5N1) | 5.4 | 18 | a b c d

ENHANCED INFLUENZA HEMAGGLUTININ BINDERS

RELATED APPLICATIONS

This application is a U.S. national phase of International Application No. PCT/US2015/021780, filed on Mar. 20, 2015, which claims priority to U.S. Provisional Application No. 61/968,874, filed Mar. 21, 2014, and U.S. Provisional Application No. 62/028,139, filed Jul. 23, 2014, all of which are incorporated by reference herein in their entirety.

FEDERAL FUNDING STATEMENT

This invention was made with government support under HDTRA1-10-1-0040 awarded by the Defense Threat Reduction Agency and U01AI074509 from the National Institutes of Health. The government has certain rights in the invention.

BACKGROUND

Influenza virus is a member of Orthomyxoviridae family. There are three subtypes of influenza viruses designated A, B, and C. The influenza virion contains a segmented negative-sense RNA genome, encoding, among other proteins, hemagglutinin (HA) and neuraminidase (NA). Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA2 protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Its surface protein hemagglutinin (HA) attaches to the sialic acid moieties on the host cell surface and mediates entry into the cell. So far, chemical analogs of the receptor have not been successful as viral-entry blockers. Current treatment options include therapeutic antibodies, small-molecules drugs and vaccination. These therapies allow protection against circulating subtypes, but may not protect against newly emerging strains. Hence, general or quickly adaptable solutions for cheap treatment options represent a constant need. Additionally, in order to rapidly diagnose early whether a patient indeed suffers from Influenza, sensitive diagnostics are desirable, as treatment at the onset of the infection have been shown to be more efficient.

Influenza presents a serious public-health challenge and new therapies are needed to combat viruses that are resistant to existing antivirals or escape neutralization by the immune system.

SUMMARY OF THE INVENTION

In a first aspect, the present invention provides polypeptides comprising or consisting of the amino acid sequence of SEQ ID NO: 1, wherein the polypeptide does not comprise the amino acid sequence of 1u84 (SEQ ID NO:5). In one embodiment, the polypeptide comprises or consists of the amino acid sequence of SEQ ID NO:2. In another embodiment, residue 46 is selected from the group consisting of R, Y, C, and W. In another embodiment, residue 46 is R. In a further embodiment, residue 46 is R and one, two, three, four, or all five of the following are true:
  (a) residue 16 is N;
  (b) residue 31 is T;
  (c) residue 33 is Q;
  (d) residue 70 is R; and
  (e) residue 71 is T.

In another embodiment, one, two, or all three of the following are true:
  (a) residue 45 is N;
  (b) residue 65 is R; and
  (c) residue 66 is L.

In a further embodiment, the polypeptide comprises a polypeptide at least 90%, 95%, 98%, 99%, or 100% identical to the amino acid sequence of SEQ ID NO:3 or SEQ ID NO:4.

In another embodiment, one, two, three, or all four of the following are true:
  (a) residue 33 is A, C, T, or S;
  (b) residue 46 is H;
  (c) residue 59 is F, W, or Y; and
  (d) residue 63 is P.

In a further embodiment, one, two, three, four, five, six, or all seven of the following are true:
  (a) residue 33 is C, S, A, T, or V;
  (b) residue 53 is a small smaller polar/charged residue;
  (c) residue 55 is S, T, or A;
  (d) residue 59 is L, P, or Y;
  (e) residue 68 is L;
  (f) residue 72 is W; and
  (g) residue 73 is E.

In another embodiment, one, two, three, or all four of the following are true:
  (a) residue 36 is K;
  (b) residue 52 is L;
  (c) residue 53 is a small polar or charged AA: and
  (d) residue 59 is Y or F.

In a further embodiment, one, two, three, or all four of the following are true:
  (a) residue 33 is P;
  (b) residue 69 is Y;
  (c) residue 70 is a polar or charged AA; and
  (d) residue 73 is E.

In another embodiment, one, two, three, four, five, six, seven, eight, nine, or all ten of the following are true:
  (a) residue 31 is any amino acid other than a charged amino acid;
  (b) residue 33 is S or T;
  (c) residue 52 is L;
  (d) residue 53 is a small polar or charged AA and is not R;
  (e) residue 59 is V;
  (f) residue 69 is a negative AA;
  (g) residue 70 is any non-positively charged AA;
  (h) residue 72 is a negative AA;
  (i) residue 73 is a negative AA; and
  (j) residue 76 is any amino acid other than R, such as a negative AA.

In a further embodiment, one, two, three, or all four of the following are true:
  (a) residue 46 is H;
  (b) residue 53 is a small polar or charged AA;
  (c) residue 63 is R; and
  (d) residue 76 is a negative AA.

In a further aspect, the present invention provides nucleic acids encoding the polypeptide of any embodiment or combination of embodiments of the invention. In another aspect, the invention provides recombinant expression vectors comprising a nucleic acid of the invention operatively linked to a suitable control sequence. In a further aspect, the invention provides recombinant host cells comprising a recombinant expression vector of the invention. In another aspect, the invention provides antibodies that selectively bind to the polypeptide of any embodiment or combination of embodiments of the invention.

In another aspect, the invention provides pharmaceutical compositions, comprising one or more polypeptides of any embodiment or combination of embodiments of the invention and a pharmaceutically acceptable carrier.

In a further aspect, the invention provides methods for treating and/or limiting an influenza infection, comprising administering to a subject in need thereof a therapeutically effective amount of one or more polypeptides of any embodiment or combination of embodiments of the invention, salts thereof, conjugates thereof, or pharmaceutical compositions thereof, to treat and/or limit the influenza infection. In one embodiment, the one or more polypeptides, salts thereof, conjugates thereof, or pharmaceutical compositions thereof are administered mucosally. In another embodiment, the mucosal administration comprises intranasal administration. In a further embodiment, the one or more polypeptides, salts thereof, conjugates thereof, or pharmaceutical compositions thereof are administered orally. In another embodiment, the subject is immune-compromised and/or is 65 years of age or older In another aspect, the invention provides methods for diagnosing an influenza infection, or monitoring progression of an influenza infection, comprising (a) contacting a biological sample from a subject suspected of having an influenza infection with a diagnostically effective amount of one or more polypeptides of any embodiment or combination of embodiments of the invention, under conditions suitable for binding of the polypeptide to a viral HA protein present in the sample; and (b) detecting polypeptide-viral HA binding complexes, where the presence of such binding complexes indicates that the subject has an influenza infection, or provides a measure progression of an influenza infection.

In a still further aspect, the invention provides methods for identifying candidate influenza vaccines, comprising contacting test compounds with one or more polypeptides of any embodiment or combination of embodiments of the invention under conditions suitable for polypeptide binding;

removing unbound test compounds; and identifying those test compounds that bind to the polypeptide of the invention, wherein such test compounds are candidate influenza vaccines.

In another aspect, the invention provides methods for identifying candidate compounds for treating, limiting, and/or diagnosing influenza infection, comprising contacting an influenza HA protein with (i) test compounds and (ii) a polypeptide of any embodiment or combination of embodiments of the invention, under conditions suitable for binding of the HA protein to the polypeptide of the present invention; and identifying those test compounds that outcompete the polypeptide for binding to the HA protein, wherein such test compounds are candidate compounds for treating, limiting, and/or diagnosing influenza infection.

Figure 5:
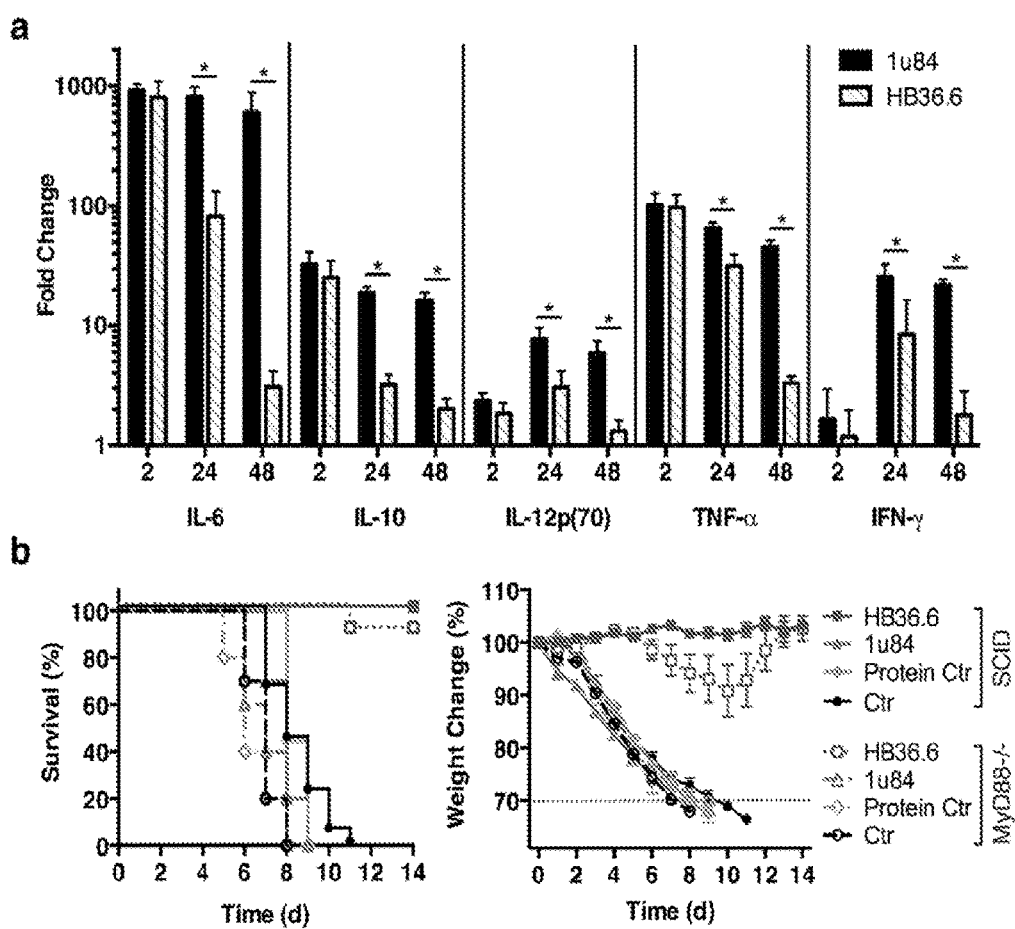
Figure 6A:
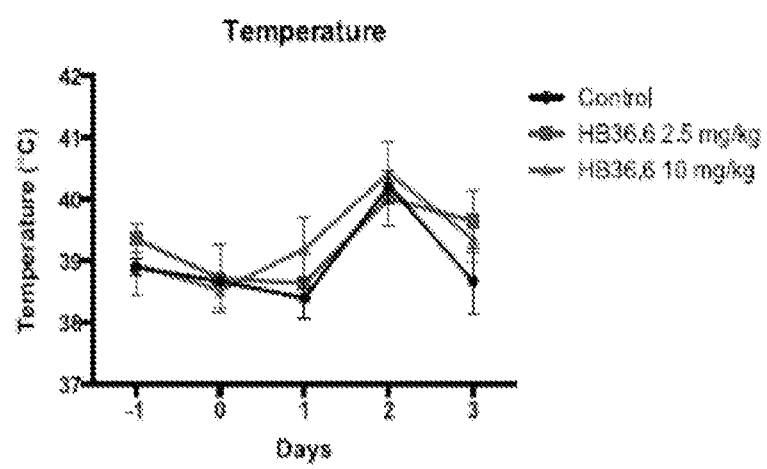
Figure 6B:
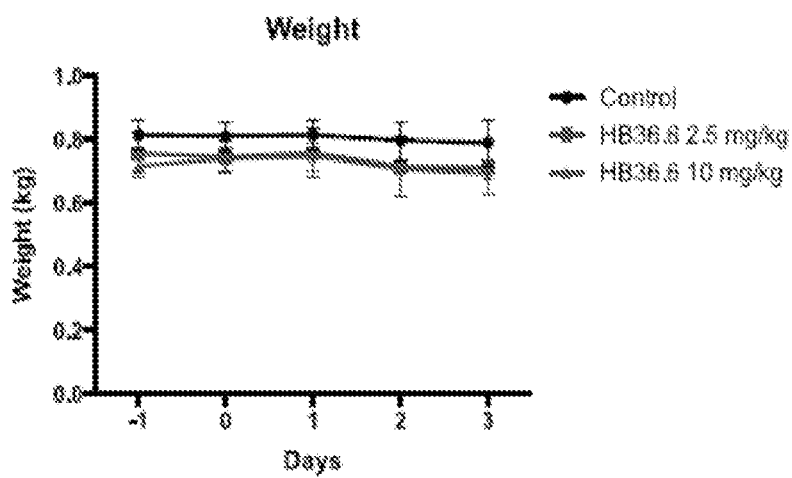
Figure 6C:
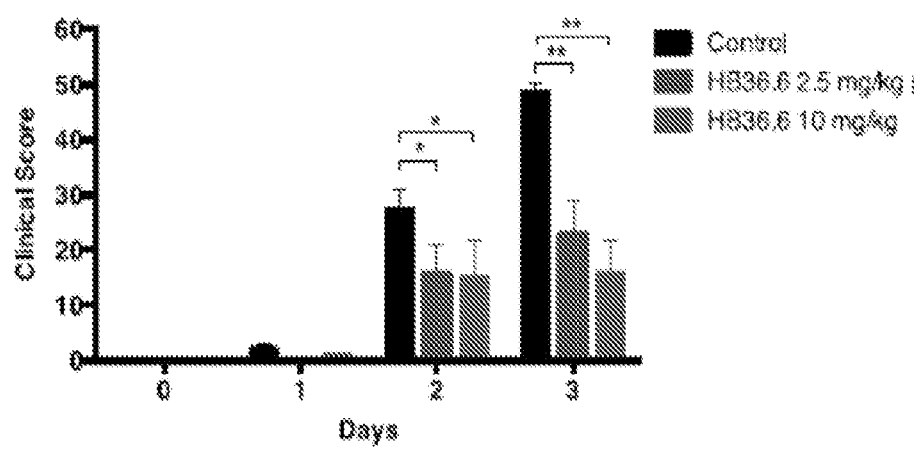
Figure 6D:
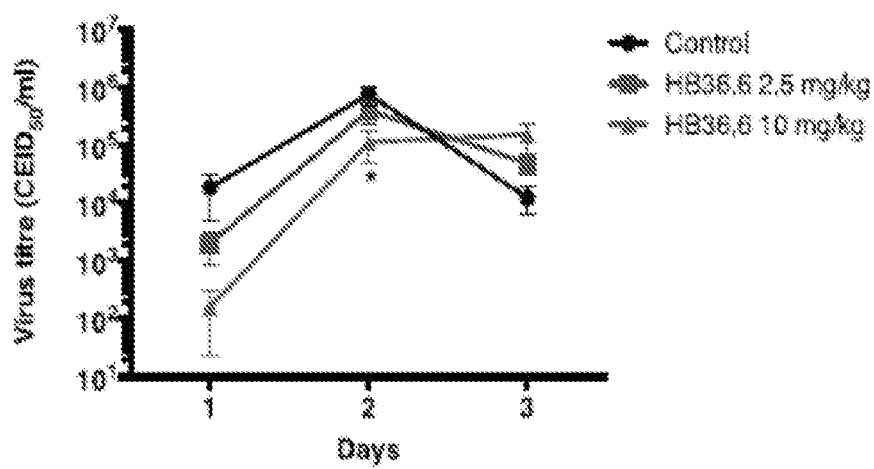

FIG. 5 HB36.6 induces a transient cytokine response that is not required for protection. (a) Inflammatory cytokines were assayed by Bio-Plex® using supernatants from lung homogenates obtained from BALB/c mice 2, 24 and 48 hours following administration with HB36.6 (6.0 mg/kg) or the scaffold protein 1u84 (6.0 mg/kg) (n≥10 mice per group). Fold change over naïve mice is shown. *P<0.05. (b) Survival and weight change in SCID and MyD88−/− mice (N=10 per group) that received 6.0 mg/kg of HB36.6, 1u84, or Protein Ctr (lysozyme) IN 2 hours before IN infection with 10 $MLD_{50}$ CA09 virus.

FIG. 6. Intranasal delivery of HB36.6 affords prophylactic protection against lethal Influenza virus challenge in mice and ferrets. (a) Temperature and (b) weight change in ferrets (N=4 per group) that received either saline buffer (Control), 2.5 or 10 mg/kg of HB36.6 administered intranasally (IN) 2 hours before aerosolized challenge with CA09 virus. (c) Clinical scores and (d) nasal wash viral titers from ferrets that received either 2.5 or 10 mg/kg of HB36.6 administered intranasally (IN) 2 hours before challenge with aerosolized CA09 virus and then were sacrificed on Day 3 post-infection. (*p<0.01, **p<0.001).

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*. 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc. Clifton. N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala: A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides an isolated polypeptide comprising or consisting of the amino acid sequence of SEQ ID NO:1, wherein the polypeptide does not comprise the amino acid sequence of 1u84. (1u84 amino acid sequence is as follows):

SNAMDGQQLNRLLLEWIGAWDPFGLGKDAYDVEAASVLQAVYETEDARTLAARIQ
SIYEFAFDEPIPFPHCLKLARRLLELKQAASCPLP (SEQ ID NO: 5))

SEQ ID NO: 1

| Position | HB36.5 or 36.6 residue | Optional residues (in addition to 36.5 or 35.6 residues) |
|---|---|---|
| 1 | S | Optional; if present, any AA |
| 2 | N | Optional; if present, any AA |
| 3 | A | Optional; if present, any AA |
| 4 | M | Optional; if present, any AA |
| 5 | D | Optional; if present, any AA |
| 6 | G | Any AA |

-continued

SNAMDGQQLNRLLLEWIGAWDPFGLGKDAYDVEAASVLQAVYETEDARTLAARIQ
SIYEFAFDEPIPFPHCLKLARRLLELKQAASCPLP (SEQ ID NO: 5))

SEQ ID NO: 1

| Position | HB36.5 or 36.6 residue | Optional residues (in addition to 36.5 or 35.6 residues) |
|---|---|---|
| 7 | Q | K and R |
| 8 | Q | S |
| 9 | L | L, K, F, D, V |
| 10 | N | Q, D, E |
| 11 | R | Polar AA, charged AA, K, or Q |
| 12 | L | Q/K/T/R |
| 13 | L | L/M/I |
| 14 | L | Polar AA |
| 15 | E | D or E |
| 16 | W; (N in 36.6) | Any AA, Q |
| 17 | I | V |
| 18 | G | Polar AA |
| 19 | A | A |
| 20 | W | W |
| 21 | D | A |
| 22 | P | P |
| 23 | F | L |
| 24 | G | G |
| 25 | L | L |
| 26 | G | G |
| 27 | K | P |
| 28 | D | N, G, H, R |
| 29 | A | A |
| 30 | Y | V |
| 31 | D (T in 36 polar); | A or N, charged AA polar AA |
| 32 | Y | R, other polar AA |
| 33 | E (Q in 36.6) | S/T/A/C/P |
| 34 | A | A |
| 35 | A | E/R |
| 36 | E | E |
| 37 | V | V |
| 38 | L | V |
| 39 | K | K |
| 40 | A | A |
| 41 | V | V |
| 42 | Y | Y |

-continued

SNAMDGQQLNRLLLEWIGAWDPFGLGKDAYDVEAASVLQAVYETEDARTLAARIQ
SIYEFAFDEPIPFPHCLKLARRLLELKQAASCPLP (SEQ ID NO: 5))

| Position | HB36.5 or 36.6 residue | SEQ ID NO: 1 Optional residues (in addition to 36.5 or 35.6 residues) |
|---|---|---|
| 43 | E | E |
| 44 | T | T |
| 45 | E; (N in 36.6) | N/S/T, H/Q |
| 46 | S; (R in 36.6) | H, T |
| 47 | A | A |
| 48 | F | F |
| 49 | D | D |
| 50 | L | L |
| 51 | A | V |
| 52 | M | M |
| 53 | R | K, D/E/N/Q/S/T |
| 54 | I | M/V |
| 55 | H | H |
| 56 | W | W |
| 57 | I | I |
| 58 | Y | F |
| 59 | N | F/Y |
| 60 | F | F |
| 61 | A | S |
| 62 | F | F |
| 63 | K | R |
| 64 | R | G, K |
| 65 | Q (R in 36.6) | R/A |
| 66 | I | I |
| 67 | P | V/N/I, K/R/Q |
| 68 | F | F |
| 69 | A | Y |
| 70 | H (R in 36.6), | Charged AA, polar AA |
| 71 | A (T in 36.6) | Any AA |
| 72 | Q | Charged AA, polar neutral AA |
| 73 | K | D/E, Polar AA |
| 74 | L (F in 36.6) | A/F |
| 75 | A | A |
| 76 | R | S/T/E/G |
| 77 | R | Q/K/E |
| 78 | L | L |

-continued

```
SNAMDGQQLNRLLLEWIGAWDPFGLGKDAYDVEAASVLQAVYETEDARTLAARIQ
    SIYEFAFDEPIPFPHCLKLARRLLELKQAASCPLP (SEQ ID NO: 5))
```

SEQ ID NO: 1

| Position | HB36.5 or 36.6 residue | Optional residues (in addition to 36.5 or 35.6 residues) |
|---|---|---|
| 79 | L | L |
| 80 | E | D |
| 81 | L | M |
| 82 | K | K |
| 83 | Q | H, R |
| 84 | A | A |
| 85 | A | H, Polar AA |
| 86 | S | Optional; if present, any AA |
| 87 | S | Optional; if present, any AA |
| 88 | P | Optional; if present, any AA |
| 89 | L | Optional; if present, any AA |
| 90 | P | Optional; if present, any AA |

The polypeptides of all aspects/embodiments of the invention bind to a conserved stem region of group 1 HA; binding of the polypeptides to the conserved stem region can be determined using binding assays as detailed in the examples that follow. The polypeptides of the invention can thus be used, for example, to treat or detect/diagnose influenza infection. An exemplary polypeptide of the invention has been extensively tested and demonstrated in the examples that follow to neutralize a wide range of genetically diverse Group 1 viruses in vitro and a single intranasal dose protects against two genetically distinct influenza strains in vivo, both therapeutically and prophylactically. No other influenza-binding peptide has ever been shown to be effective in vivo. Also, in contrast to antibody-based therapeutics, polypeptide binding to the HA stem is alone sufficient for highly effective in vivo protection against influenza, without activation of antibody-dependent cellular cytotoxicity.

The polypeptides of the invention also provide a cheaper, more selective alternative to currently used hemagglutinin binding antibodies, which are costly to produce. The polypeptides of the invention can also be used for in vivo biosensing applications, whereas the antibodies cannot because of their structurally necessary disulfide bonds and difficulty to express robustly.

As disclosed in the examples that follow, exemplary HA-binding polypeptides of the invention have been identified and subjected to extensive mutational analysis against a variety of viral strains. These studies have identified residues where modifications are tolerated, and where they may lead to additional functionality. In vitro testing via deep mutational scanning shows that a number of these mutations lead to increased binding specificity against distinct subtypes of influenza, which could be highly useful in a diagnostic role or for therapeutic use against existing, new, or emerging strains of influenza. Such modifications may comprise, for example, conservative amino acid substitutions. Some residues can be substituted with any amino acid, and thus the "alternative residues" noted in the Tables herein are listed as "any amino acid." Other positions can only tolerate conservative substitutions, and thus the "alternative residues" for these positions will define one or more amino acid grouping, as noted in the Tables herein. These amino acid groupings are defined as follows:

Polar AA's: H, N, Q, Y, T, S, and C;
Hydrophobic AA's: A, I, L, V, M, F, W, P, and G;
  Aliphatic AA's (subset of hydrophobic AA's): A, I, L, V, and M;
  Aromatic AA's (subset of hydrophobic AA's): Y, W, and F;
Charged AA's: K, R, D, E, and H:
  Basic/Positive AA's (subset of charged AA's): K and R; and
  Acidic/Negative AA's (subset of charged AA's): D and E.
Small AAs: G, T, S, C, A, V, I, L
Large AAs: M, F, W, Y, R, H, K As will be understood by those of skill in the art, the polypeptides may contain additional residues as deemed appropriate for an intended use. In one non-limiting embodiment, the polypeptides may include an optional methionine residue at the N-terminus; such a residue may be present, for example, when the polypeptides are expressed recombinantly and the nucleic acid encoding the polypeptide encodes an N-terminal methionine residue to facilitate expression. An N-terminal methionine residue is not required for activity, and thus is not required in the polypeptides of the invention, which can also be made via standard polypeptide synthesis techniques. In the examples that follow, the polypeptides include an N-terminal methionine residue, and thus all residue numbering in the examples is shifted by one compared to the polypeptides recited herein (i.e.: residue 1 in SEQ ID NO:1 will be residue 2 in the polypeptides in the examples, residue 2 in SEQ ID NO:1 will be residue 3 in the polypeptides in the examples, etc.)

In one embodiment, the isolated polypeptide comprises or consists of the amino acid sequence of SEQ ID NO:2.

| SEQ ID NO: 2 | |
|---|---|
| Position | |
| 1 | Optional; if present, any AA |
| 2 | Optional; if present, any AA |
| 3 | Optional; if present, any AA |
| 4 | Optional; if present, any AA |
| 5 | Optional; if present, any AA |
| 6 | G |
| 7 | Q |
| 8 | Q |
| 9 | L |
| 10 | N |
| 11 | R |
| 12 | Charged AA, I |
| 13 | L |
| 14 | Charged AA |
| 15 | E |
| 16 | Any AA other than W (N in 36.6) |
| 17 | I |
| 18 | G |
| 19 | A |
| 20 | W |
| 21 | Charged AA, M, A |
| 22 | P |
| 23 | F; hydrophobic AA |
| 24 | G; small AA |
| 25 | L; hydrophobic AA, neutral AA (not C) |
| 26 | G; small AA |
| 27 | K; Any AA |
| 28 | D |
| 29 | A |
| 30 | Y |
| 31 | D; Charged AA (T in 36.6) |
| 32 | Y |
| 33 | E; S, T (Q in 36.6) |
| 34 | A; small AA |
| 35 | A; small AA |
| 36 | E |
| 37 | V; A, I, L |
| 38 | L; A, I, L |
| 39 | E |
| 40 | A |
| 41 | V, L |
| 42 | Y; large AA |
| 43 | D, T, S |
| 44 | T |
| 45 | E; (N in 36.6) |
| 46 | S; polar AA, aromatic AA (R in 36.6) |
| 47 | A; S, T |
| 48 | F |
| 49 | D; N |
| 50 | L |
| 51 | A, V |
| 52 | M, V, L |
| 53 | K |
| 54 | I, M, V |
| 55 | H |
| 56 | W |
| 57 | I |
| 58 | Y; hydrophobic AA |
| 59 | F, Y |
| 60 | F; T |
| 61 | A; G |
| 62 | F |
| 63 | K; R, P |
| 64 | R; G |
| 65 | A, R (R in 36.6) |
| 66 | I; Any AA (L in 36.6) |
| 67 | V, L, I, R, Q, N |
| 68 | F |
| 69 | A; hydrophobic AA, charged AA, polar AA |
| 70 | H; charged AA (R in 36.6) |
| 71 | S, T, L, K (T in 36.6) |
| 72 | Q, T, R |
| 73 | K; Q |

| SEQ ID NO: 2 | |
|---|---|
| Position | |
| 74 | L, A, F (F in 36.6) |
| 75 | A |
| 76 | R; K |
| 77 | R; K |
| 78 | L |
| 79 | L |
| 80 | E; Charged AA |
| 81 | L |
| 82 | K |
| 83 | Q, H, K |
| 84 | A |
| 85 | A; H |
| 86 | Optional; if present, any AA |
| 87 | Optional; if present, any AA |
| 88 | Optional; if present, any AA |
| 89 | Optional; if present, any AA |
| 90 | Optional; if present, any AA |

In another embodiment, residue 46 of SEQ ID NO:1 or 2 is selected from the group consisting of R, Y, C, and W; in a further embodiment, residue 46 of SEQ ID NO:1 or 2 is R. In another embodiment of SE ID NO:1 and 2, residue 46 is R and one or more of the following is true:

(a) residue 16 is N;

(b) residue 31 is T;

(c) residue 33 is Q;

(d) residue 70 is R; and (e) residue 71 is T.

In another embodiment that can be combined with any of the above embodiments, one or more of the following is true:

(a) residue 45 is N;

(b) residue 65 is R; and (c) residue 66 is L.

In another embodiment, the isolated polypeptide comprises or consists of a polypeptide at least 90%, 95%, 98%, 99%, or 100% identical to the amino acid sequence of SEQ ID NO:3 or SEQ ID NO:4.

HB36:6

(SEQ ID NO: 3)
(SNAMD)GQQLNRLLLEnIGAWDPFGLGKDAYtYqAAEVLKAVYETnrA
FDLAMRIHWIYNFAFKRrIPFArtQKIARRLLELKQAA(SSPLP)
(SEQ ID NO: 3)

HB36.5:

(SEQ ID NO: 4)
(SNAMD)GQQLNRELLEWIGAWDPFGLGKDAYDYEAAEVLKAVYETESA
FDLAMRIHWIYNFAFKRQIPFAHAQKLARRLLELKQAA(SSPLP);

where the residues in parentheses are optionally present.

Figure 2:
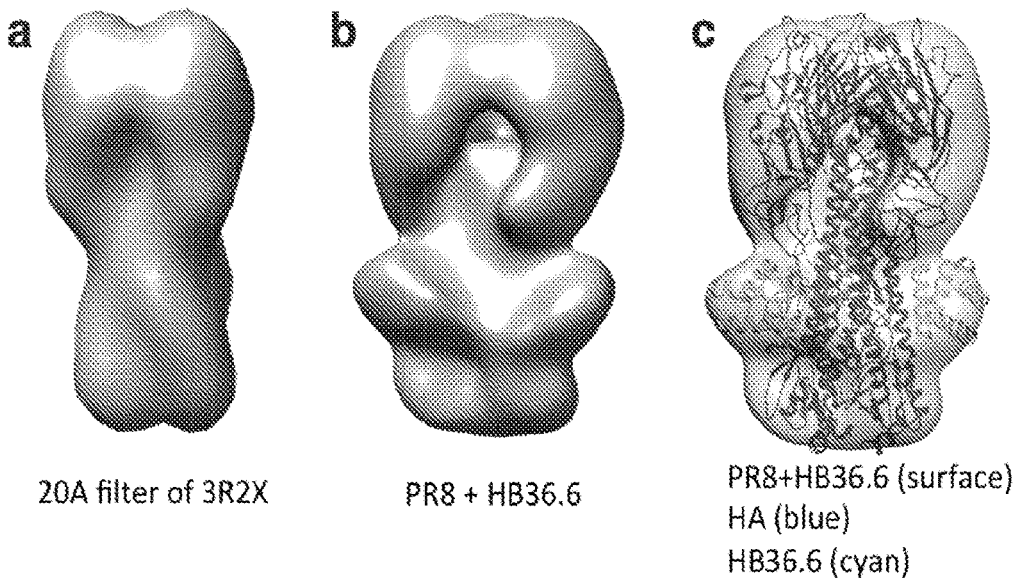
FIG. 2 Characterization of HB36.6. (a) Crystal structure of PR8 HA (derived from PDB 3R2x) filtered to 20 Å resolution. (b) Negative stain EM reconstruction of PR8 HA bound to HB36.6. (c) X-ray structure of PR8 HA (PDB 3R2x) and model of HB36.6 docked into EM reconstruction in b. HB36.6 fits well into the extra density in the stem region. (d) Equilibrium binding constants determined by biolayer interferometry for HB36.5 and HB36.6 against six HAs demonstrate broad improvements against a variety of Group 1 strains. (e) $EC_{50}$ (µg/ml), compound concentration that reduces viral replication by 50%, of HB36.6 and Ribavirin against five representative Group 1 strains. ND: not determined.

Biolayer Interferometry (BLI) of exemplary peptides of the invention (HB36.6 and HB36.5) has shown them to be broadly cross-reactive against many Group I Hemagglutinin (HA) subtypes including pandemic 2009 California H1N1. For example, peptide HB36.6 has a Kd against pandemic 2009 California H1N1 of 3.1 nM, 5-fold tighter than any known de novo binder; and roughly 6-fold stronger than HB36.5 (FIG. 2d). Exemplary peptide of the invention HB36.6 has been shown to possess in vivo prophylactic and therapeutic activity, as demonstrated in detail in the examples that follow, with increased specificity against H1 strains.

In another embodiment, one, two, three, or all four of the following are true with respect to the polypeptide comprising SEQ ID NO: 1 or 2 (or SEQ ID NO: 1 or 2 wherein residue 46 is selected from the group consisting of R, Y, C, and W; or is R):
(a) residue 33 is A, C, T, or S;
(b) residue 46 is H;
(C) residue 59 is F, W, or Y; and
(d) residue 63 is P.

Polypeptides according to this embodiment showed increased specificity for strain A/California/7/2009 H1N1 via deep mutational scanning.

In another embodiment, one, two, three, four, five, six, or all seven of the following are true with respect to the polypeptide comprising SEQ ID NO: 1 or 2 (or SEQ ID NO:1 or 2 wherein residue 46 is selected from the group consisting of R, Y, C, and W; or is R):
(a) residue 33 is C, S. A. T, or V;
(b) residue 53 is a small smaller polar/charged residue;
(c) residue 55 is S, T, or A;
(d) residue 59 is L, P, or Y;
(e) residue 68 is L;
(f) residue 72 is W: and
(g) residue 73 is E.

Polypeptides according to this embodiment showed increased specificity for strain A/Adachi/2/1957 H2N2 via deep mutational scanning.

In another embodiment, one, two, three, or all four of the following are true with respect to the polypeptide comprising SEQ ID NO: 1 or 2 (or SEQ ID NO: 1 or 2 wherein residue 46 is selected from the group consisting of R, Y, C, and W: or is R):
(a) residue 36 is K;
(b) residue 52 is L;
(c) residue 53 is a small polar or charged AA; and
(d) residue 59 is Y or F.

Polypeptides according to this embodiment showed increased specificity for strain A/Indonesia/05/2005 H5N1 via deep mutational scanning.

In another embodiment, one, two, three, or all four of the following are true with respect to the polypeptide comprising SEQ ID NO: 1 or 2 (or SEQ ID NO:1 or 2 wherein residue 46 is selected from the group consisting of R, Y, C, and W; or is R):
(a) residue 33 is P;
(b) residue 69 is Y;
(c) residue 70 is a polar or charged AA; and
(d) residue 73 is E.

Polypeptides according to this embodiment showed increased specificity for strain A/Vietnam/1203/2004 H5N1 via deep mutational scanning.

In another embodiment, one, two, three, four, five, six, seven, eight, nine, or all ten of the following are true with respect to the polypeptide comprising SEQ ID NO:1 or 2 (or SEQ ID NO:1 or 2 wherein residue 46 is selected from the group consisting of R, Y, C, and W; or is R):
(a) residue 31 is any amino acid other than a charged amino acid;
(b) residue 33 is S or T;
(c) residue 52 is L;
(d) residue 53 is a small polar or charged AA and is not R;
(e) residue 59 is V;
(f) residue 69 is a negative AA;
(g) residue 70 is any non-positively charged AA;
(h) residue 72 is a negative AA;
(i) residue 73 is a negative AA; and
(j) residue 76 is any amino acid other than R, such as a negative AA.

Polypeptides according to this embodiment showed increased specificity for strain A/turkey/Wisconsin/1966 H9N2 via deep mutational scanning.

In another embodiment, one, two, three, or all four of the following are true with respect to the polypeptide comprising SEQ ID NO:1 or 2 (or SEQ ID NO:1 or 2 wherein residue 46 is selected from the group consisting of R, Y, C, and W: or is R):
(a) residue 46 is H;
(b) residue 53 is a small polar or charged AA;
(c) residue 63 is R, and
(d) residue 76 is a negative AA.

Polypeptides according to this embodiment showed increased specificity for strain A/duck/Alberta/60/1976 H12N5 via deep mutational scanning.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In a further embodiment, the polypeptides of any embodiment of any aspect of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used diagnostically to, for example, assess if a subject has been infected with influenza virus or monitor the development or progression of an influenza virus infection as part of a clinical testing procedure to, e.g., determine the efficacy of a given treatment regimen. However, they may also be used for other detection and/or analytical and/or diagnostic purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such as $^{33}P$, $^{32}P$, $^{35}S$, $^{3}H$, and $^{125}I$. Polypeptides of the invention can be attached to radionuclides directly or indirectly via a chelating agent by methods well known in the art.

When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also be attached to solid supports, which are particularly useful for in vitro assays or purification of influenza virus or HA protein. Such solid supports might be porous or nonporous, planar or nonplanar and include, but are not limited to, glass, cellulose, polyacrylamide, nylon, polystyrene, polyvinyl chloride or polypropylene supports. The polypeptides can also, for example, usefully be conjugated to filtration media, such as NHS-activated Sepharose or CNBr-activated Sepharose for purposes of affinity chromatography. They can also usefully be attached to paramagnetic microspheres, typically by biotin-streptavidin interaction. The microspheres can be used for isolation of influenza virus or HA protein from a sample containing influenza virus or HA protein. As another example, the polypeptides of the invention can usefully be attached to the surface of a microtiter plate for ELISA.

The polypeptides of the invention can be fused to marker sequences to facilitate purification. Examples include, but are not limited to, the hexa-histidine tag, the myc tag or the flag tag.

The polypeptides of the invention can be conjugated to an antigen recognized by the immune system of a subject to which the polypeptide is administered. Conjugation methods for attaching the antigens and polypeptide are well known in the art and include, but are not limited to, the use of cross-linking agents. The polypeptide will bind to the influenza virus HA protein and the antigen will initiate a T-cell attack on the conjugate that will facilitate destruction of the influenza virus.

In another embodiment of any aspect herein, the present invention provides retro-inverso polypeptides corresponding to the polypeptides of the invention. Retro-inverso polypeptides of the invention comprise or consist of D-amino acids assembled in a reverse order from that of L-sequence polypeptide versions of the polypeptides disclosed above, thus maintaining the overall topology of the polypeptide, and maintaining HA binding.

In another aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a further aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989*: Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique,* $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a further aspect, the present invention provides antibodies that selectively bind to the polypeptides of the invention. The antibodies can be polyclonal, monoclonal antibodies, humanized antibodies, and fragments thereof, and can be made using techniques known to those of skill in the art. As used herein, "selectively bind" means preferential binding of the antibody to the polypeptide of the invention, as opposed to one or more other biological molecules, structures, cells, tissues, etc., as is well understood by those of skill in the art.

In another aspect, the present invention provides pharmaceutical compositions, comprising one or more polypeptides of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other active agents suitable for an intended use, including but not limited to anti-HA and anti-NA antibodies.

In a further aspect, the present invention provides methods for treating and/or limiting an influenza infection, comprising administering to a subject in need thereof a therapeutically effective amount of one or more polypeptides of the invention, salts thereof, conjugates thereof, or pharmaceutical compositions thereof, to treat and/or limit the influenza infection. When the method comprises treating an influenza infection, the one or more polypeptides are administered to a subject that has already been infected with the influenza virus, and/or who is suffering from symptoms (including but not limited to chills, fever, sore throat, muscle pains, coughing, weakness, fatigue, and general discomfort) indicating that the subject is likely to have been infected with the influenza virus. As used herein. "treat" or "treating" means accomplishing one or more of the following: (a) reducing influenza viral titer in the subject; (b) limiting any increase of influenza viral titer in the subject; (c) reducing the severity of flu symptoms; (d) limiting or preventing development of flu symptoms after infection; (e) inhibiting worsening of flu symptoms; (f) limiting or preventing recurrence of flu symptoms in subjects that were previously symptomatic for influenza infection.

When the method comprises limiting an influenza infection, the one or more polypeptides are administered prophylactically to a subject that is not known to have been infected, but may be at risk of exposure to the influenza virus. As used herein, "limiting" means to limit influenza infection in subjects at risk of influenza infection. Given the nature of seasonal influenza outbreaks, virtually all subjects are at risk of exposure, at least at certain times of the year. Groups at particularly high risk include children under age 18, adults over the age of 65, and individuals suffering from one or more of asthma, diabetes, heart disease, or any type of immunodeficiency.

While not being bound by any mechanism of action, it is believe that prophylactic protection by the polypeptides of the invention appears to be mediated by limiting or blocking viral replication at the respiratory site of exposure whereas therapeutic protection may be achieved by curtailing the spread of the virus into the lower respiratory tract and limiting inflammation and disease.

In one embodiment, the subject is immune-compromised (including, but not limited to, subjects taking immunosuppressants, subjects with a disease that compromises the immune system, such as acquired immune deficiency syndrome, etc.) and/or is 65 years of age or older. As shown in the examples that follow, the therapeutic and prophylactic activity of the polypeptides of the invention is not dependent on the subject having a properly functioning immune system, and thus the methods are of particular benefit from any subject that does not have a properly functioning immune system.

The methods of the invention can be used to treat any individual infected with influenza virus, including but not limited to influenza virus A.

As used herein, a "therapeutically effective amount" refers to an amount of the polypeptide that is effective for treating and/or limiting influenza infection. The polypeptides are typically formulated as a pharmaceutical composition, such as those disclosed above, and can be administered via any suitable route, including orally, by inhalation spray, ocularly, in dosage unit formulations containing conventional pharmaceutically acceptable carriers, adjuvants, and vehicles. In one particular embodiment, the polypeptides are administered mucosally, including but not limited to intraocular or intranasal administration. In another particular embodiment, the polypeptides are administered orally. Such particular embodiments can be administered via droplets, nebulizers, sprays, or other suitable formulations.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the invention neutralize influenza virus infectivity. While not being limited by any mechanism of action, neutralizing activity may be achieved by inhibiting fusion of the influenza virus and the membrane of the targeted cell, including a membrane of an intracellular compartment, such as an endosome. In various embodiments, the polypeptides of the invention prevent influenza virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by influenza virus in the absence of the polypeptides. Neutralization can, for instance, be measured as described in "Laboratory techniques in influenza," edited by F.-X. Meslin, M. M. Kaplan and H. Koprowski (1996), 4th edition. Chapters 15-17. World Health Organization, Geneva.

The polypeptides according to the invention can bind to the HA protein with any suitable affinity constant ($K_d$ value) that provides therapeutic or prophylactic benefit. In various embodiments, the $K_d$ value is lower than $0.2*10^{-4}$ M, $1.0*10^{-5}$ M, $1.0*10^{-6}$ M, $1.0*10^{-7}$ M, $1.0*10^{-8}$ M, $1.0*10^{-9}$M, $1.0*10^{-10}$ M, $1.0*10^{-11}$ M, or $1.0*10^{-12}$ M. Affinity constants can for instance be measured using surface plasmon resonance, i.e., an optical phenomenon that allows for the analysis of real-time biospecific interactions by detection of alterations in protein concentrations within a biosensor matrix, for example, using the BIACORE system (Pharmacia Biosensor AB, Uppsala, Sweden).

The polypeptides made be administered as the sole prophylactic or therapeutic agent, or may be administered together with (i.e.: combined or separately) one or more other prophylactic or therapeutic agents, including but not limited to oseltamivir, zanamivir, and laninamivir.

In another aspect, the present invention provides methods for diagnosing an influenza infection, or monitoring progression of an influenza infection, comprising
   (a) contacting a biological sample from a subject suspected of having an influenza infection with a diagnostically effective amount of one or more polypeptides of the invention under conditions suitable for binding of the polypeptide to a viral HA protein present in the sample;
   (b) removing unbound polypeptide and/or sample; and
   (c) detecting polypeptide-viral HA binding complexes, where the presence of such binding complexes indicates that the subject has an influenza infection, or provides a measure progression of an influenza infection.

The methods of this aspect of the invention can be used to more accurately identify patients that may be suffering from an influenza infection and to thus provide more informed determination of treatment options by an attending caregiver. Individuals at risk of an influenza infection are as described above. The methods can also be used to monitor progression of an influenza infection; in this embodiment, the subject is known to be infected, and the methods can be used, for example, as a data point for an attending caregiver to determine whether to initiate, modify, or continue a particular course of therapy, such as treatment with neuraminidase or M2 protein inhibitors.

The biological sample may be any suitable biological sample including, but not limited to blood, serum, nasal secretions, tissue or other biological material from a subject at risk of infection.

The sample may first be manipulated to make it more suitable for the method of detection. "Manipulation" includes, but is not limited to treating the the sample in such a way that any influenza virus in the sample will disintegrate into antigenic components such as proteins, polypeptides or other antigenic fragments. The polypeptides of the invention are contacted with the sample under conditions which allow the formation of an complex between the human polypeptides and influenza virus or antigenic components thereof that may be present in the sample. The formation of such complexes, if any, indicating the presence of influenza virus in the sample, is then detected and measured by suitable means. Such methods include, but are not limited to homogeneous and heterogeneous binding immunoassays, such as radioimmunoassays (RIA), ELISA, immunofluorescence, immunohistochemistry. FACS, BIACORE and Western blot analyses. Suitable conditions to promote binding of the test compounds to one or more polypeptide of the invention can be determined by those of skill in the art, based on the teachings herein.

The polypeptides of the invention for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. In one embodiment, conditions are selected to identify test compounds that bind to the polypeptide of the invention with a $K_d$ value lower than $0.2*10^{-4}$ M, $1.0*10^{-5}$ M, $1.0*10^{-6}$ M, $1.0*10^{-7}$ M, $1.0*10^{-8}$ M, $1.0*10^{-9}$ M, $1.0*10^{-10}$ M, $1.0*10^{-11}$ M, or $1.0*10^{-12}$ M.

In a further aspect, the present invention provides methods for identifying candidate influenza vaccines, comprising
   (a) contacting test compounds with a polypeptide of the present invention under conditions suitable for polypeptide binding, and
   (b) identifying those test compounds that bind to the polypeptide of the invention, wherein such test compounds are candidate influenza vaccines.

As discussed above, the polypeptides of the present invention were designed to target the conserved stem region of HA. Thus, the polypeptides of the invention can be viewed as specific binders to an HA epitope, similar to antibody binding to a specific epitope. Vaccines can be produced, for example, by selecting small molecules (ie: mimotopes) that bind to an antibody specific to a viral epitope. Thus, the present methods involve substituting one or more polypeptides of the present invention for the antibody in such assay to identify candidate influenza vaccines.

Suitable conditions to promote binding of the test compounds to one or more polypeptide of the invention can be determined by those of skill in the art, based on the teachings herein. The polypeptides of the invention for use in this aspect may comprise a conjugate as disclosed above, to provide a tag useful for any detection technique suitable for a given assay. The tag used will depend on the specific detection/analysis/diagnosis techniques and/or methods used, as discussed above. The methods may be carried in solution, or the polypeptide(s) of the invention may be bound or attached to a carrier or substrate, as discussed above. Based on the teachings herein, it is within the level of skill in the art to determine specific conditions for the various types of diagnostic assays disclosed in this aspect of the invention. In one embodiment, conditions are selected to identify test compounds that bind to the polypeptide of the invention with a $K_d$ value lower than $0.2*10^{-4}$ M, $1.0*10^{-5}$M, $1.0*10^{-6}$M, $1.0*10^{-7}$M, $1.0*10^{-8}$M, $1.0*10^{-9}$ M, $1.0*10^{-10}$ M, $1.0*10^{-11}$ M, or $1.0*10^{-12}$M.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be produced by any suitable means, such as chemical synthesis. The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

In another aspect, the present invention provides methods for identifying candidate compounds for treating, limiting, and/or diagnosing influenza infection, comprising
(a) contacting an influenza HA protein with (i) test compounds and (ii) a polypeptide of the present invention, under conditions suitable for binding of the HA protein to the polypeptide of the present invention; and
(b) identifying those test compounds that outcompete the polypeptide for binding to the HA protein, wherein such test compounds are candidate compounds for treating, limiting, and/or diagnosing influenza infection.

In this aspect, the methods identify test compounds that compete with the polypeptides of the invention for binding to HA, and thus such candidate compounds may be useful in any of the other methods of the invention disclosed herein. Any suitable test compound can be used, as disclosed above in the eleventh aspect of the invention.

In general, competitive inhibition is measured by means of an assay, wherein an HA composition is admixed with the polypeptide(s) of the invention and the test compounds to be screened. In one embodiment, the test compounds to be screened are present in excess. Protocols based upon ELISAs are suitable for use in such competition studies. In certain embodiments, one may pre-mix the polypeptide(s) of the invention with varying amounts of test compounds to be screened (e.g., 1:10, 1:20, 1:30, 1:40, 1:50, 1:60, 1:70, 1:80, 1:90 or 1:100) for a period of time prior to applying to the HA composition. In other embodiments, the polypeptide(s) of the invention and varying amounts of test compounds to be screened are admixed during exposure to the HA composition. Any suitable detection means can be used binding. In one embodiment, the polypeptide(s) of the invention are tagged for detection, as discussed above. In this embodiment, the detectable label will decrease in the presence of competitive test compounds. The reactivity of the (labeled) polypeptide of the invention in the absence of test compound could serve as one suitable control. Preferably, competitive test compounds will, when present in excess, inhibit specific binding of the polypeptide(s) of the invention to HA by at least 10%, preferably by at least 25%, more preferably by at least 50%, and most preferably by at least 75% to 90% or even greater.

Exemplary conditions for HA binding studies can be carried out as disclosed in the examples that follow.

All of these aspects/embodiments disclosed herein can be combined with any other aspect/embodiment, unless the context clearly dictates otherwise.

Example 1

Influenza is a major public health threat, and pandemics, such as the 2009 H1N1 outbreak, are inevitable. The influenza envelope glycoprotein hemagglutinin (HA) is found on the surface of the influenza virus and consists of a highly variable globular head domain (HA1) and a more conserved stem domain (HA2)[1,2]. Influenza viruses comprise two phylogenetic groups (Groups 1 and 2) consisting of 18 influenza subtypes and numerous genetic variants or strains within each subtype. Vaccination can prevent influenza infection but current vaccines are strain specific, providing little or no protection against drifted or shifted strains[3-5].

Here we show that even in the absence of Fc, intranasal administration of an HA stem binding protein interferes with influenza replication in vivo and provides strong protection from infection when administered as a prophylactic or as a therapeutic. We further show that protection is independent of a host immune response demonstrating a unique mechanism for disrupting influenza infection in vivo via direct binding of the HA stem without engaging the host immune system.

Results

HA Stem Binding Protein Affords Fc-Independent Prophylactic and Therapeutic Protection Against Influenza In Vivo.

Figure 1:
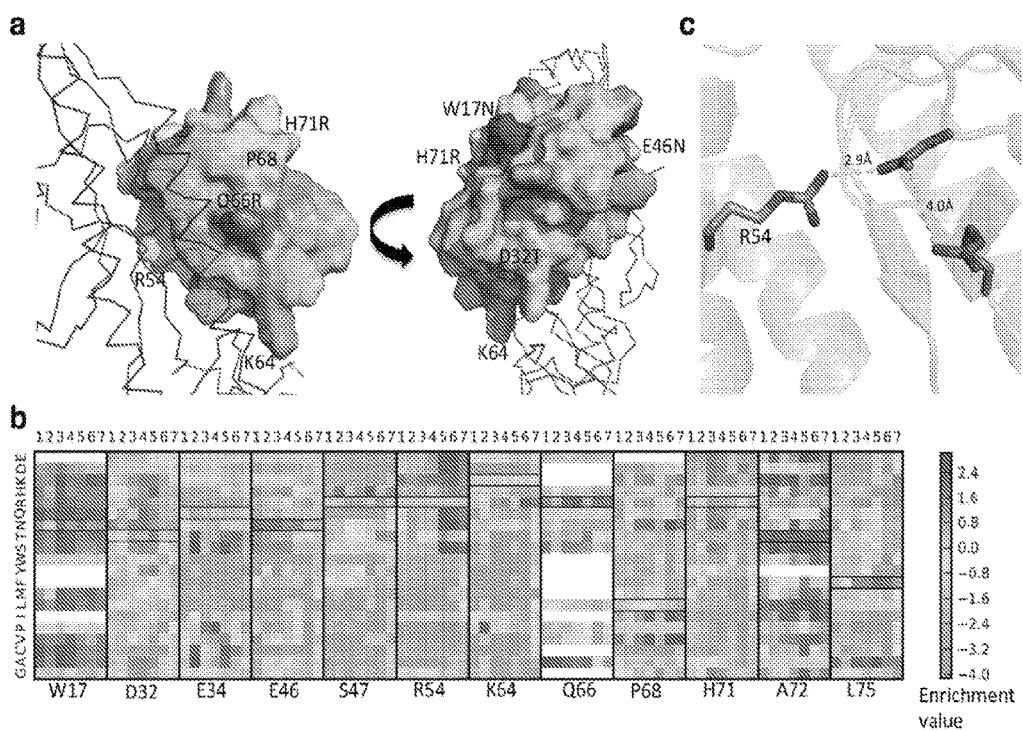
FIG. 1 HA subtype selections reveal both specificity-enhancing mutations and overall affinity-increasing substitutions. (a) HB36.5, in complex with HA, colored by average residue enrichment in FACS sorts against 7 different HA subtypes. Residues that were mutated to obtain HB36.6 are labeled in black. (b) Enrichment of substitutions at 12 key positions in HB36.5 in selections against each HA strain. Labels at the bottom indicate position in HB36.5; numbers at the top represent the different flu strains (Subtype 1: A/South Carolina/l/1918, 2: A/California/04/2009, 3: A/Vietnam/203/2004, 4: A/Indonesia/05/2005, 5: A/Adachi/2/1957, 6: A/turkey/Wisconsin/1/1966, 7: A/duck/Alberta/60/1976). At most positions, the enrichment profiles against the different HA strains are similar, but at several positions they are quite distinct. At Arg54, for example, the arginine is highly conserved in selections for binding against HAs 1-4, but is outcompeted by smaller charged/polar residues in selections against HAs 5-7 (red region at upper right of R54 panel). White cells indicate insufficient data (<15 sequences in the input library); black boxes indicate the residue identities in HB36.6. (c) Origin of HA strain dependence of substitutions at HB36.5 position R54. R54 forms salt bridges with Asp and Arg residues in HAs 1-4. In HAs 5-7, the Asp is mutated to a Glu, disrupting the salt bridge with Arg54 leading to a preference for smaller polar residues.

We started by modifying a stable, broadly cross-reactive HA binding protein, HB36.5, for increased affinity against multiple HA subtypes. We constructed a library in which each amino acid was individually mutated to all other possible amino acids, carried out two rounds of yeast display selection against seven different Group 1 HA subtypes, sequenced the initial library and the libraries after the first and second sorts, and computed the enrichment (or depletion) of each individual point mutant during affinity maturation. The core of the binding interface was highly conserved in the selections against the different HA subtypes (FIG. 1a), but several second shell mutations were enriched across all seven subtypes (FIG. 1a; FIG. 1b). Multiple subtype-specific substitutions were also identified around the periphery of the binding interface (FIG. 1b), which reflect HA sequence differences near the interface (FIG. 1c). We made a combinatorial library of substitutions that were enriched across all subtype selections at a total of 12 mutated positions and subjected it to three rounds of yeast display sorting against A/South Carolina/1/918 (H1N1) HA, which converged on a variant with nine substitutions called HB36.6. Negative-stain electron microscopy revealed that HB36.6 binds in the designed location on HA (FIG. 2a-c). BioLayer® interferometry showed that HB36.6 had higher affinity than HB36.5 against all tested subtypes, with greater than 40-fold and 10-fold affinity increases for H2 and H5 respectively (FIG. 2d).

In vitro, HB36.6 potently neutralized a wide range of genetically distinct human (H1N1) and avian (H5N1) influenza viruses (range of genetic diversity between HA sequences is 64-89%) with a 50% effective concentration ($EC_{50}$) range of 0.18-12.0 μg/ml (FIG. 2e). In contrast, Ribavirin, a broad-spectrum antiviral[13], has an $EC_{50}$ range of 15-18 μg/ml against a representative subset of the same influenza strains. These results show that HB36.6 neutralizes a wide range of genetically distinct influenza viruses in vitro with greater potency than a small molecule influenza antiviral.

Figures 3A, 3B, 3C:
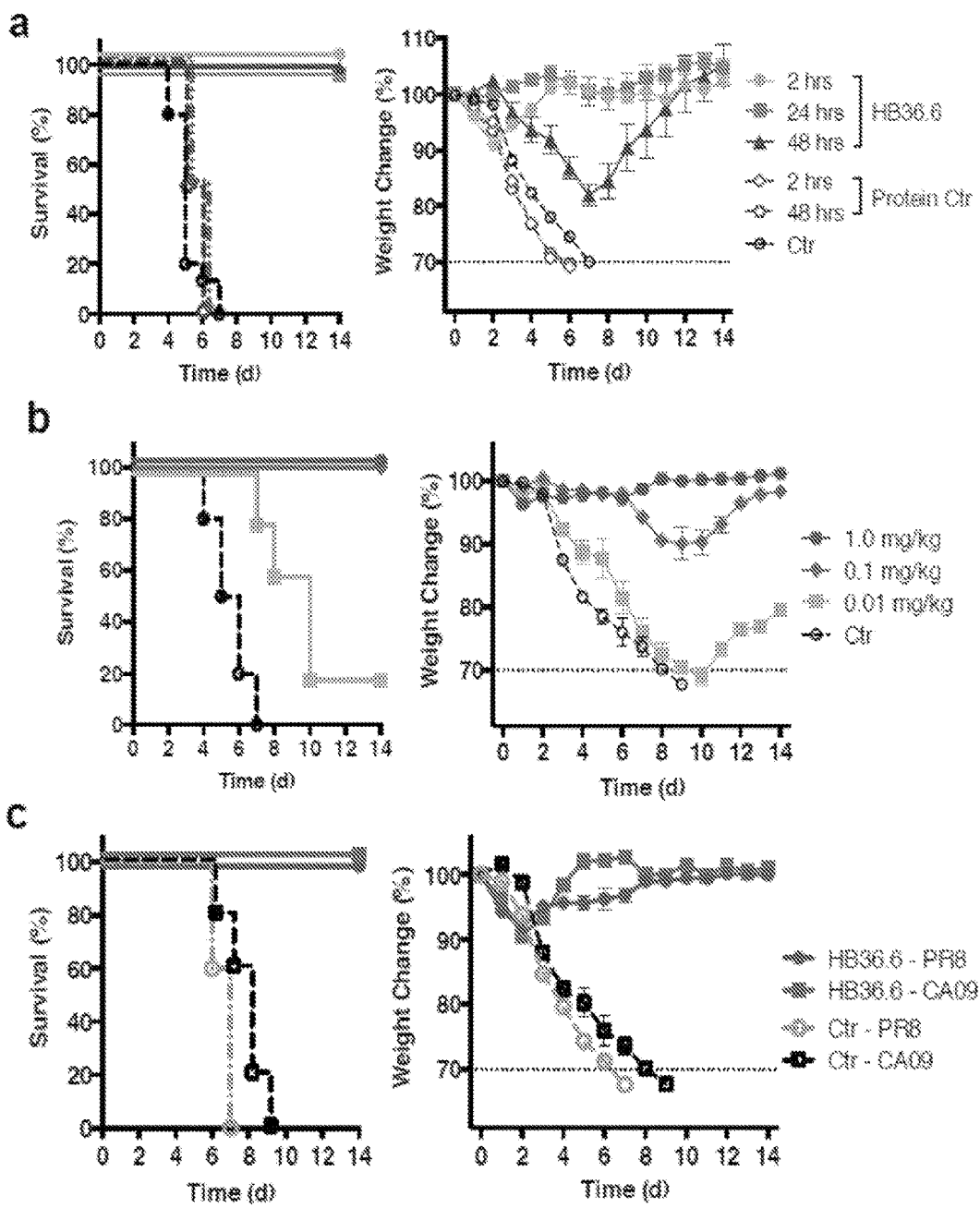
FIG. 3 Intranasal delivery of HB36.6 affords prophylactic and therapeutic protection against lethal Influenza virus challenge. (a) Survival and weight change in BALB/c mice (N=10 per group) that received 6.0 mg/kg of HB36.6 administered intranasally (IN) at 2, 24, or 48 hours before challenge with 10 $MLD_{50}$ CA09 virus. The Protein Ctr group received 6.0 mg/kg of lysozyme at 2 or 48 hours before challenge with 10 $MLD_{50}$ CA09 virus. (b) Survival and weight change in BALB/c mice (N=5 per group) that received 0.01-1 mg/kg IN doses of HB36.6 2 hours before challenge with 10 $MLD_{50}$ of CA09 virus. (c) Survival and weight change in BALB/c mice (N=5 per group) that received 3.0 mg/kg of HB36.6 IN 2 hours before IN infection with 10 $MLD_{50}$ of H1N1 CA09 virus or 6 $MLD_{50}$ H1N1 A/PR/8/34 (PR8). (d) Survival and weight change in BALB/c mice (N=10 per group) that received 3.0 mg/kg of HB36.6 IN on day 0 (2 hours post-infection) or +1, +2, or +3 days post-infection (d.p.i.) or once daily on days +1-4 post-infection with 10 $MLD_{50}$ CA09 virus. (e) Survival and weight change in BALB/c mice (n=10 per group) that were challenged with 3 $MLD_{50}$ of CA09 virus and then received either a single dose of HB36.6 (0.1-10 mg/kg) IN on day +1 p.i., or Oseltamivir (2.5 mg/kg/dose) by oral gavage twice a day on days +1-5 p.i. (10 doses total). Mean and SEM are shown.

To determine if HB36.6 can protect against influenza infection in vivo, we gave BALB/c mice a single intranasal (IN) dose of 6.0 mg HB36.6/kg body-weight mouse at 2, 24, or 48 hours prior to challenge with a lethal dose (10 times the 50% mouse lethal dose or 10 $MLD_{50}$) of H1N1 A/California/07/2009 (CA09) virus, a highly virulent Group 1 pandemic influenza strain that leads to rapid weight loss and death in mice within 4-8 days post-infection (p.i.). When administered up to 48 hours before challenge, a single pre-exposure dose of HB36.6 afforded complete protection with 100% survival and moderate to low weight loss whereas all untreated controls (Ctr) exhibited >30% weight loss and no survival (FIG. 3a). The protection was specific to HB36.6 since a protein control (lysozyme, 6.0 mg/kg), administered either 48 or 2 hrs before CA09 challenge provided no protection and resulted in weight loss and mortality comparable to the controls (FIG. 3a). The same dose of HB36.6 delivered intravenously (IV) provided no protection (data not shown). Lower doses of 1.0, 0.1, and 0.01 mg/kg administered IN two hours prior to lethal challenge with CA09 also resulted in 100% survival with little (0.1 mg/kg) or no (1.0 mg/kg) weight loss whereas controls exhibited rapid weight loss and succumbed to the infection within 7 days p.i. (FIG. 3b). Mice that received the lowest dose tested (0.01 mg/kg) exhibited weight loss, yet survived 2-3 days longer than controls and 20% of mice recovered and survived.

To determine if HB36.6 can provide broad protection against genetically distinct strains in vivo, we inoculated mice IN with HB36.6 (3.0 mg/kg) two hours before challenge with either CA09 or A/PR8/34 (PR8), a highly virulent H1N1 mouse-adapted influenza virus that is 18% divergent from CA09. FIG. 3c shows that HB36.6 provided the same degree of protection against PR8 with 100% of the mice surviving and no weight loss. This result is consistent with the in vitro results showing that HB36.6 broadly binds Group 1 HAs (FIG. 2d,e).

Figures 3D, 3E:
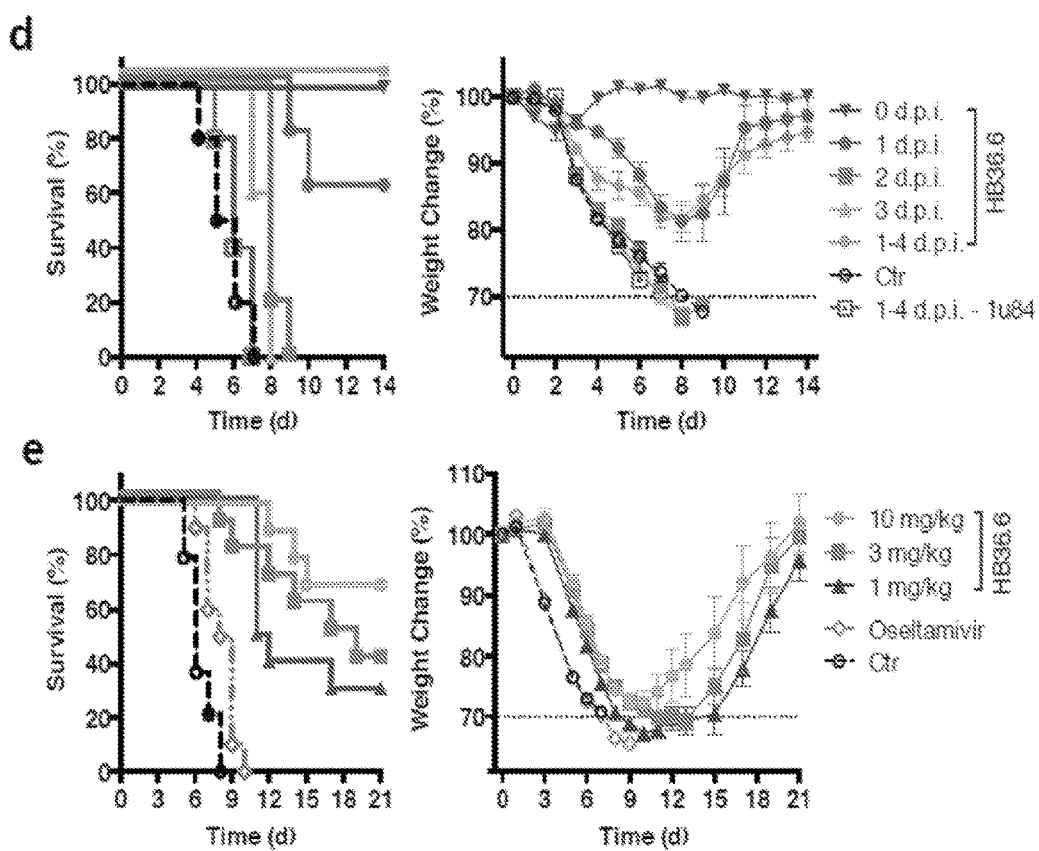

We next investigated HB36.6 as a post-exposure prophylactic. We challenged mice with CA09 virus and then treated with either a single IN dose of 3.0 mg/kg HB36.6 on day 0 (2 hours p.i.), +1, +2 or +3 p.i. or four daily IN doses administered on days +1-4 p.i. HB36.6 reduced weight loss and afforded complete recovery and protection from lethality in 100% of mice when administered daily for 4 days or as a single inoculation administered 2 hours p.i. or 60% protection from lethality when administered +1 day p.i. (FIG. 3d). There was no significant difference in protection from weight loss between mice receiving daily doses on days +1-4 p.i. or a single dose at 2 hours or day +1 p.i. suggesting that a single dose within 1 day post-exposure is sufficient to protect from disease. Although mice that received HB36.6 at day +2 or +3 p.i. eventually succumbed to their infection, a single dose at these later time-points also provided a benefit in that the majority of these mice succumbed at day 8 or 9 p.i. whereas 100% of the controls succumbed within 4-7 days p.i. (2 d.p.i., p=0.0006; 3 d.p.i, p=0.0031 compared to controls) (FIG. 3d). The protection observed was specific for HB36.6 binding to the HA since daily administration of the scaffold protein (PDB ID 1u84) that HB36.6 is modeled on provided no protection (FIG. 3d).

We next compared a single dose of HB36.6 to the approved antiviral, oseltamivir (Tamiflu®, Roche). We challenged mice with CA09 virus and then treated with either a single IN dose of HB36.6 (1.0-10 mg/kg) on day +1 p.i., or oseltamivir (5 mg/kg/day) by oral gavage, twice daily for 5 days starting on day +1 p.i. A single dose of HB36.6 resulted in an increase in the number of survivors and delayed the mean day of death in animals that died from the infection (FIG. 3e). The highest rate of survival (70%) was observed in the group treated with the highest dose of HB36.6 (10 mg/kg), and a dose-responsive effect was observed. In comparison, oseltamivir was not able to prevent mortality (0% survival), but did significantly delay the time to death by about 2.5 days compared to controls (p<0.001). These results indicate that a single dose of HB36.6 provides superior protection against influenza than the leading influenza antiviral oseltamivir.

Figure 4:
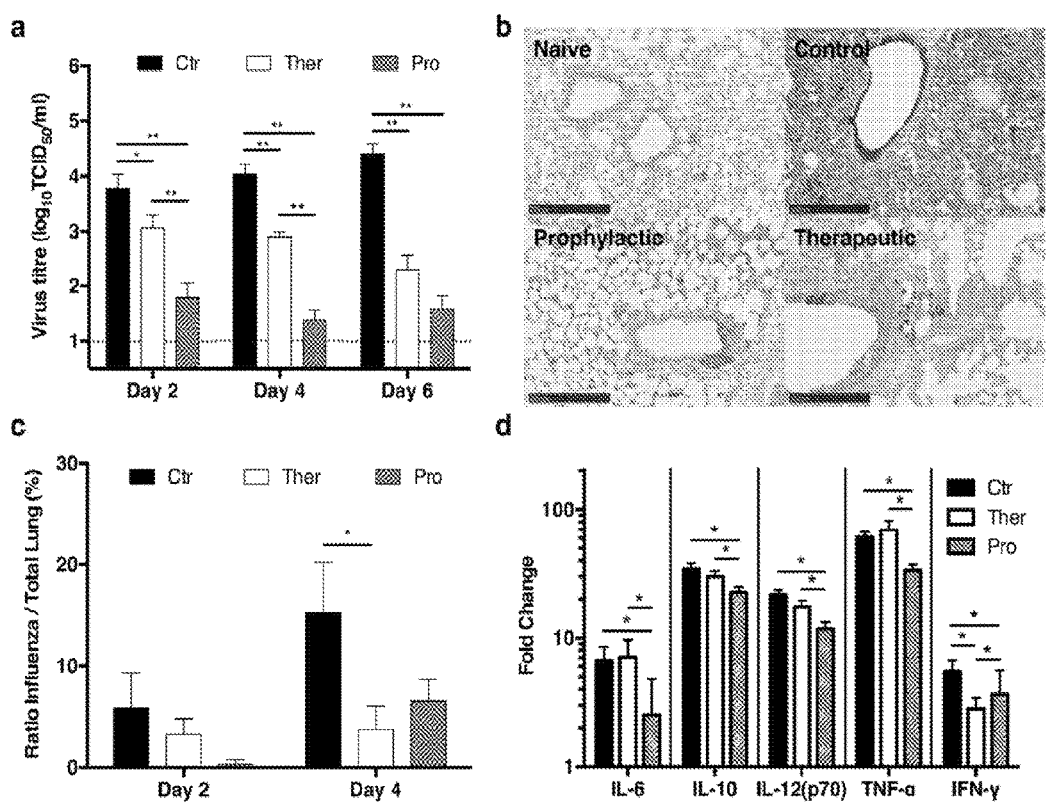
FIG. 4 HB36.6 suppresses viral replication and inflammation in the lung. (a) Viral titers in nasal washes of untreated infected controls (Ctr) and mice that received 6.0 mg/kg HB36.6 either 1 day before (Prophylaxis, Pro) or 1 day after (Therapeutic, Ther) infection with 10 $MLD_{50}$ CA09 virus. Nasal washes collected on days 2, 4 and 6 post-infection were measured by determining the 50% tissue culture infectious dose ($TCID_{50}$) (bars indicate mean viral titer ±SD, n≥18 mice per group). (b) IHC staining of intracellular influenza NP (H1N1) of representative lung sections from uninfected (naïve) and untreated control and HB36.6 treated mice (Prophylactic and Therapeutic) at 4 days post-infection with 10 $MLD_{50}$ CA09 virus. (c) Quantification of influenza positive cells in lung tissues was performed by measuring the area of positive staining compared to the total tissue on the slide (uniform random sampling of 50% lung tissue). (d) Inflammatory cytokines were assayed by Bio-Plex® using supernatants from lung homogenates obtained from BALB/c mice on day 2 following infection with 10 $MLD_{50}$ CA09 virus (n≥8 mice per group). Shown is fold change over naïve-uninfected mice. For a, c and d, significant differences between the Pro and Ther groups to the Ctr group are shown: *P<0.05, **P<0.001.

To determine the effects of HB36.6 at the respiratory sites of virus exposure, we analyzed viral replication and inflammation in nasal and lung compartments in mice that received a single IN dose of HB36.6 (6.0 mg/kg) either 24 hours before (Prophylactic-Pro) or after (Therapeutic-Ther) challenge with CA09. We collected nasal washes on days 2, 4, and 6 post-challenge and viral titers were measured by an end-point dilution assay ($TCID_{50}$). At each time-point p.i., mice treated with HB36.6 before (Pro) or after (Ther) challenge exhibited a substantial 1-3 log-fold reduction in mean viral titers when compared to untreated controls, with the lowest viral loads consistently observed in the prophylactic group (FIG. 4a). These results indicate that prophylaxis with HB36.6 likely afforded protection from infection by binding and blocking the virus at the respiratory site of exposure whereas therapy with HB36.6 may afford protection by containing the burst of viral replication that precedes progression to disease and death.

We next investigated the effects of HB36.6 on viral replication in the lung. We treated mice IN with HB36.6 (6.0 mg/kg) 1 day before or post-infection with CA09 and then collected lung tissue on day 2 and 4, which we stained for intracellular expressed influenza nucleoprotein (NP) to identify infected cells. Lung tissues from mice that received prophylactic or therapeutic administration of HB36.6 showed significantly less viral replication in the lungs when compared to the untreated controls at both day 2 (not shown) and day 4 p.i. (FIG. 4b) and in situ enumeration of NP positive cells in the lung tissue confirmed there were a significantly lower number of infected cells in the lungs at day 4 in mice that received HB36.6 as a therapeutic when compared to controls (P≤0.0263, FIG. 4c). Thus, therapeutic administration of HB36.6 reduced viral replication in the lung (FIG. 4c) and nasal passages (FIG. 4a) as early as day 2 p.i. with the greater suppression of viral replication relative to controls observed in the lung (FIG. 4c) supporting the possibility that therapeutic protection was mediated by reducing the spread of viral replication into the lung. To determine if IN delivery of HB36.6 penetrates into the lower respiratory tract, mice received 6.0 mg/kg of FLAG-tagged HB36.6 and 6 hours later, lung tissue was sectioned and stained using anti-FLAG antibodies. The protein was readily detected throughout the lung tissue (data not shown) indicating HB36.6 is able to penetrate into the lower respiratory tract.

Influenza infection results in the expression of pro-inflammatory cytokines that induce inflammation and recruit activated immune cells to clear the infection. However, this inflammatory response damages the pulmonary epithelium and increases susceptibility to secondary infections by ~100 fold[14,15]. To determine if HB36.6 protects from influenza-induced inflammation, mice received a single IN dose of HB36.6 (6.0 mg/kg) either 24 hrs before (Pro) or 24 hrs after (Ther) lethal challenge with CA09. Lungs were collected on day 2 p.i. and supernatants from lung homogenates were analyzed for the expression of inflammatory cytokines (IL-6, IL-10, IL-12p70, TNF-α, IFN-γ). HB36.6 delivered either as a prophylactic or therapeutic did not significantly increase the cytokine response and in fact several cytokines were significantly lower than in the controls (P≤0.00119, FIG. 4d). These results support the possibility that the reduction in viral loads by HB36.6 provided additional benefits in also decreasing the cytokine responses that lead to increased inflammation and tissue damage. Together, these results show that HB36.6 blocks and interferes with viral spread, resulting in a lower viral replication, suppression of the cytokine response and decreased lung inflammation. Furthermore, since HB36.6 lacks Fc, these results show that, in contrast to monoclonal antibodies that bind the same HA stem site, engagement of the host FcγR is not required for protection in vivo.

HA Stem Binding Protein does not Induce a Protective Host Antiviral Response

Small proteins, such as HB36.6, may stimulate an immune response that could interfere with the effectiveness of a second administration or alternatively, stimulate antiviral responses that can contribute to protection[16]. To determine if repeat dosing induces an immune response against HB36.6 that could interfere with the potency of subsequent dosing, we administered 4 consecutive doses (3.0 mg/kg dose) of HB36.6 IN spaced two weeks apart. Two weeks after each dose, blood was collected and the serum analyzed by ELISA for the presence of binding antibodies against HB36.6. No antibodies against HB36.6 were detected after the 1st and 2nd dose but by 3rd dose, low levels of antibody responses were detected in 4 of the 10 animals. Importantly, a lethal challenge with CA09 24 hours after the 4th dose still provided 100% protection from mortality and morbidity (data not shown). These results indicate HB36.6 is poorly immunogenic, and low levels of antibody that may be induced following repeated dosing of HB36.6 does not interfere with its protective efficacy.

Induction of even a modest adaptive antibody response suggested HB36.6 likely stimulated a host innate response. To determine if HB36.6 administration induces antiviral cytokine responses that could contribute to protection, cytokines were measured at different time-points post-HB36.6 administration. Mice received a single IN dose of HB36.6 (6.0 mg/kg) or 1u84 (6.0 mg/kg) and lungs were collected 2, 24 or 48 hrs post-administration. Supernatants from lung homogenates were analyzed for the expression of inflammatory cytokines (IL-6, IL-10, IL-12p70, TNF-α, IFN-γ). Both HB36.6 and 1u84 induced low levels of cytokines that peaked between 2-24 hrs post-administration and by 48 hrs the levels had dropped to pre-administration levels (FIG. 5a). Importantly, cytokine levels after HB36.6 administration were significantly lower than levels induced by 1u84 that afforded no protection from challenge. These data suggest that, although administration with HB36.6 induced a cytokine response, the levels were too transient and/or low to contribute to protection.

To investigate the possibility that HB36.6 may induce other host responses that could contribute to protection, we tested HB36.6 for protection against influenza in two severe immune-deficient mouse models: NOD SCID gamma (SCID) and MyD88−/− mice. SCID mice lack mature T, B, and NK cells are unable to develop an adaptive immune response[17,18]. MyD88−/−, mice lack TLR signaling and are deficient in cytokine signaling, resulting in a severely dampened innate and adaptive immune response[19-21]. HB36.6 (6.0 mg/kg), 1u84 (6.0 mg/kg), and a protein control (lysozyme, 6.0 mg/kg) were IN administered 2 hrs before challenge with CA09. HB36.6 protected 100% of the SCID mice and 90% of the MyD88−/− mice with only minimal weight loss (FIG. 5b), whereas all control mice (1u84, Protein, and Naïve) exhibited significant weight loss and 0% survival in both SCID and MyD88−/− mice. The ability of HB36.6 to afford protection in two severely immune-compromised mouse models provide further evidence that the antiviral effect of HB36.6 is due to direct binding of the HA stem and is independent of an antiviral host response or engagement of the FcγR.

DISCUSSION

We show that HB36.6, exemplary of the polypeptides of the present invention, is able to neutralize a wide range of genetically diverse Group 1 viruses in vitro and a single intranasal dose protects against two genetically distinct influenza strains in vivo indicating that the broad specificity of HB36.6 observed in vitro may translate to broad protection in vivo. Prophylactic protection by IN-administered HB36.6 appears to be mediated by limiting or blocking viral replication at the respiratory site of exposure whereas therapeutic protection is likely achieved by curtailing the spread of the virus into the lower respiratory tract and limiting inflammation and disease. Furthermore, a single dose of HB36.6 in mice outperformed a five-day, ten dose regimen of oseltamivir, the lead antiviral approved for the treatment of influenza in humans. In contrast to some bNAbs, we found that HB36.6 protects against influenza independent of engagement with the FcγR and activation of antibody-dependent cellular cytotoxicity (ADCC)[1,9]. Thus, in contrast to mAb, HB36.6 binding to the HA stem is alone sufficient for highly effective in vivo protection against influenza. Inhaled delivery of HB36.6 may result in higher concentrations of binder at the respiratory site of infection than can be achieved by antibodies, which are generally administered via an intravenous route.

We found that HB36.6 induced lower cytokine responses than its non-protective scaffold protein and showed no loss in protective efficacy when tested in two severe immune-deficient mouse models. Taken together these results provide strong evidence that HB36.6 mediates protection independent of the host response and primarily through direct binding of the HA stem. Since post-exposure inflammation mediates enhanced influenza disease and increased susceptibility to secondary infections[14], the ability of HB36.6 to afford protection without inducing an inflammatory response suggests it could be used to increase resistance against influenza without exacerbating disease due to inflammation.

The ability of HB36.6 to provide protection independent of a host immune response or FcγR interactions implies that a properly functioning immune system is not required for efficacy. This possibility has significant implications for further development of proteins like HB36.6 as a new class of antivirals for protecting the immune-compromised or elderly, which comprise the majority of deaths from seasonal influenza each year[22].

Methods

Yeast Display kD Titrations.

Wild type HB36.5 and the transformed HB36.5 SSM yeast display library was inoculated into 1 mL of SDCAA medium supplemented with carbenicillin and chloramphenicol and grown overnight at 30° C. 250 rpm. Cells were pelleted by centrifugation, resuspended in 200 μL of SGCAA, 40 μL of the resuspended cells were inoculated into 960 additional μL of complete SGCAA and induced ~24 h at 18° C., 250 rpm. Cells were collected by centrifugation, washed with PBSF (PBS, 0.1% w/v BSA) and diluted to $OD_{600}$ of 2.0, $1.5\times10^5$ cells were mixed with purified biotinylated hemagglutinin (HA) in PBSF individually at a range of concentrations spanning the construct's predicted $k_D$ and incubated at 22° C. for 30 m. After labeling with HA, the cells were collected by centrifugation, washed once with PBSF, and incubated with 0.6 μL of FITC-labeled anti-CMyc antibody and 0.25 μL phycoerythrin (PE)-labeled streptavidin on ice for 10 m. Cells were collected, washed with PBSF, and resuspended into 200 μL of PBSF. Fluorescence of 50,000 cells from each titration point was measured on an Accuri C6 flow cytometer with a 488 nm laser for excitation and a 575 nm band pass filter for emission. Negative controls for binding were induced cells with no HA labeling. BD Cflow software was used to measure the total PE fluorescence of the displaying cell population and a custom MATLAB non-linear curve fitting script was used to derive equilibrium binding constants for each hemagglutinin subtype.

Site-Saturation Mutagenesis Library Construction.

HB36.5 in pETCON® plasmid was mutagenized individually via Kunkel's method[23] in 86 consecutive codon positions using NNK degenerate primers purchased from Integrated DNA Technologies (Coralville. Iowa). Primers were designed using Firnberg's method. The theoretical library size of all 86 reactions was 1720 amino acid sequences. Kunkels reactions were purified with QiaQuick® columns (Qiagen, Hilden, Germany) and pooled in groups of 12 (codon positions 1-12, 13-24, 25-36, 37-48, 49-60, 61-72, 73-86), 1 μL of each plasmid pool was transformed by electroporation into XL10 Gold electrocompetent cells (Stratagene, La Jolla, Calif.) with a minimum efficiency of $3\times10^5$ CFUs per pool (>100-fold coverage). Liquid cultures were grown overnight in TB and harvested using a QiaPrep® miniprep kit (Qiagen, Hilden, Germany). Mutated genes were amplified from each plasmid pool by adding 1 μL of plasmid to 10 μL of 5× Phusion® Buffer, 1 μL of 10 mM dNTPs, 2.5 μL of 10 μM upGS primer, 2.5 μL of 10 μM downCMyc® primer, and 0.5 μL of Phusion® polymerase in 50 μL total volume. The reaction used 30 cycles of PCR (98° C. 10 s, 65° C. 15 s, 72° C. 15 s). PCR product was purified with a QiaQuick® kit and transformed into EBY100 *S. cerevisiae* using Chao's method[24] along with gel-purified pETCON® vector digested with NdeI/XhoI (NEB, Waltham, Mass.).

Yeast Display HA Selections.

Transformed HB36.5 SSM yeast display library was sorted in two rounds. For each round, cells were grown in 10 mL of SDCAA overnight at 30° C. collected by centrifugation, and induced in SGCAA at 18° C. for ~24 hours. Cells were collected by centrifugation, washed with PBSF, and $\sim4\times10^6$ cells labeled with purified biotinylated HA at a concentration half of the $k_D$ determined by yeast display titrations or, if no $k_D$ could be determined, 500 nM. In the first round of sorting, primary labeling proceeded for 30 m at 22° C. as described for titrations. In the second round, to select for mutations that improved binding but did not destabilize the protein, primary labeling was performed for 30 m at 37° C. Secondary labeling was done with 1.2 μL anti-CMyc FITC and 0.5 μL SAPE in a total volume of 100 μL PBSF on ice for 10 m. In each sorted population, the top ~5% of FITC-displaying cells were collected.

Illumina Sequencing.

Plasmid DNA was prepared as previously described[11]. Genes were amplified from the plasmid by adding 36.5 μL of purified plasmid to 10 μL of 5× Phusion master mix, 1 μL each of pETCON®_inner_fwd and pETCON®_inner_rev, 1 μL of 10 mM dNTPs, and 0.5 μL of Phusion® polymerase (Thermo). The reaction used 30 cycles of PCR (98° C. 10 s, 58° C. 15 s, 72° C. 15 s). Correctly sized products were gel extracted using a Qiaquick® gel extraction kit (Qiagen), 10 μL of gel extracted reaction product were added to 10 μL of 5× Phusion® master mix, 1 μL each of miseq_outer_fwd and miseq_outer_rev with the correct library barcode, 1 μL of 10 mM dNTPs, and 0.5 μL of Phusion® polymerase in 50 μL, and amplified again with 30 cycles of PCR (98° C. 10 s, 58° C. 15 s, 72° C. 15 s). The two primer sets have overhangs that add Illumina sequencing primer binding sites, barcode sequences, and flow cell adaptors to the gene to be sequenced. They additionally add 12 entirely degenerate bases at the beginning of the forward and reverse read, ensuring adequate diversity for the Illumina basecalling algorithms. This enabled the DNA pools to be prepared and sequenced in two runs of paired-end 251 bp mode on an Illumina MiSeq®, (Illumina, San Diego, Calif.) using a standard MiSeq® kit and protocols. Pools were mixed to have 6.5% of the total loaded DNA from the unselected pool, 6.5% of the total loaded DNA from each first-round selected pool, and 3.25% from each second-round selected pool, with 35% Illumina PhiX control DNA to increase diversity and data quality.

DMS Data Processing.

Raw sequence files were processed into fastq format, split by barcode, allowing up to 1 mismatch, and adapter sequence was removed using Illumina OLB 1.9.4. Split library sequences were processed using scripts from Enrich 0.2 to yield mutation counts in each library. Counts for each sorted library were converted to log 2 enrichment relative to the unselected library using custom scripts. Enrichment value was calculated by linear regression of enrichment for each individual substitution at each round. The slope of the regressed line is the enrichment value[25].

Combinatorial Library Construction and Selection.

Twelve positions in HB36.5 that contained substitutions highly enriched against many or all tested subtypes were mutated in a combinatorial library with a total sequence diversity of $10^8$. This library was constructed using recursive PCR assembly, as described below, with the only difference being that the assembly oligos contained degenerate codons designed using GLUE[26] to maximize enriched amino acid codon representation. This library was transformed into yeast using Chao's method[24] with an efficiency around $10^7$, and sorted by three rounds of yeast display for binding to A/South Carolina/1/1918 HA until sequence convergence was achieved. The final converged sequence, which we name HB36.6, had 9 total mutations relative to HB36.5.

Recursive PCR Assembly.

The gene for HB36.6 with 40 bp of additional pET-FLAG® overlap sequence, to allow homologous recombination, was assembled via recursive PCR. Sequences were designed using DNAWorks®[27] and purchased from Integrated DNA Technologies, Inc. (Coralville, Iowa). The outermost two primers were diluted to 5 μM and mixed, while the inner primers were diluted to 0.5M and mixed. A 10 μL volume of outer primer mix was added to 12.7 μL of inner primer mix, along with 1 μL of 10 mM DNTPs, 6 μL of 5× Phusion: buffer, and 0.3 μL of Phusion® polymerase (NEB, Waltham, Mass.) for a final volume of 30 μL. Product was assembled with 30 rounds of PCR (98° C. 30 s, 58° C. 30 s, 72° C. 30 s). A second round of PCR was used to further amplify correctly assembled product. A 1.25 μL aliquot of the first PCR reaction product was added to S 5 μL of 5× Phusion® Buffer, 0.75 μL 10 mM DNTPs, 2 μL of outer primer mix, and 0.25 μL of Phusion® polymerase in 25 μL. The same PCR conditions were used for a further 30 rounds and the product was purified using a QiaQuick® PCR cleanup kit (Qiagen, Hilden, Germany) and eluted in EB. Gibson assembly[28] was used to insert the assembled gene into gel-purified pETFLAG® vector digested with NdeI/XhoI (NEB, Waltham, Mass.). A 1.5 μL aliquot of cut vector at 20 ng/μL was added to 1 μL of assembled gene and 7.5 μL of Gibson enzyme mix (all enzymes from NEB, Waltham, Mass.). The reaction was incubated at 50° C. for 1 h and 2 μL was transformed into 20 μL of XL10 Gold chemically competent *E. coli* and plated onto a kanamycin agar plate. Plasmid sequences were confirmed by colony PCR and Sanger sequencing, and colonies with correctly assembled plasmid were grown in TB and harvested using a QiaPrep® miniprep kit (Qiagen, Hilden, Germany).

Protein Expression and Purification.

HB36.6 in a pETFLAG vector was expressed in Rosetta2 (DE3) *E. coli* cells. HB36.6 used throughout these studies contained the FLAG tag (DYKDDDDK (SEQ ID NO: 6)). Cells were grown in 500 μL aliquots of MDG non-inducing media supplemented with kanamycin at 37° C. 250 rpm overnight. Each vial was used to inoculate 500 mL of ZYM-5052 auto-induction media[29], which was grown for ~48 hours at 22° C., 250 rpm. Cells were harvested by centrifugation and resuspended in 25 mL of lysis buffer (50 mM Tris, 300 mM NaCl, 30 mM imidazole, pH 8.2) with half of a dissolved complete, EDTA-free protease inhibitor tablet (Roche, Basel, Switzerland) and supplemented with DNAse and lysozyme at ~1 mg/mL. Resuspended cells were lysed via sonication with a Qsonica® Q500 (Fisher Scientific, Hampton, N.H.) at 70% power for 10 minutes (20 s on/20 s off) on ice. Insoluble cell debris was removed by centrifugation for 30 m at 40,000 g. Supernatant was applied to gravity-flow columns containing 2.5 mL of Ni-NTA resin (Qiagen, Hilden, Germany) pre-equilibrated with lysis buffer. Protein was washed with 25 mL wash buffer (50 mM Tris, 300 mM NaCl, 75 mM imidazole, pH 8.2) and eluted with 10 mL elution buffer (50 mM Tris, 300 mM NaCl, 300 mM imidazole, pH 8.2). Protein was concentrated to ~20 mg/mL using a Vivaspin 10 kD MWCO centrifugal concentrator (Sartorius Stedim, Goettingen, Germany) at 4000 g. Imidazole was removed by dialysis (2×4 L buffer) into 50 mM Tris, 300 mM NaCl, pH 8.2 at 4° C. Concentration was determined by absorbance at 280 nm on a NanoDrop® spectrophotometer (Thermo Scientific, Waltham, Mass.) using extinction coefficients calculated from amino acid sequences. For in vivo experiments, proteins were further processed using bacterial endotoxin removal beads (Miltenyi Biotec, San Diego, Calif.).

Circular Dichroism Spectroscopy.

Purified proteins were tested for folding and denaturation temperature using an Aviv 420 circular dichroism spectrometer (Aviv Biomedical, Lakewood, N.J.). Protein was diluted to 0.6 mg/mL in PBS and CD absorbance was measured at 205 nm at 25° C. Absorbance was characteristic of a structured α-helical protein. To test the thermal denaturation temperature of HB36.6, absorbance at the 222 nm α-helix peak was measured in 2° increments between 15° and 95° C.

Protease Resistance Assays.

Proteins to be tested were diluted to 1 mg/mL in PBS and Gibco 0.25% trypsin/phenol red (Life Technologies. Carlsbad, Calif.) was diluted to 0.005% in PBS. Equal parts protein solution and trypsin were mixed and incubated at 37° C. Time points were taken by removing 6 μL aliquots of solution, mixing with 6 μL of 2×SDS loading buffer (100 mM Tris, 4% SDS, 0.2% bromphenol blue, 20% glycerol, pH 6.8) and incubating for 2 m at 85° C. Denatured aliquots were stored at −20° C. until being loaded on a 12% NuPage® Bis-Tris gel (Life Technologies, Carlsbad, Calif.) and run at 150V in 1×MES buffer (50 mM MES, 50 mM Tris Base, 0.1% SDS, 1 mM EDTA, pH 7.3). Negative controls were one lane with undigested protein and one lane with trypsin but no test protein. Gels were scanned and bands were quantified using ImageJ. Band size as a percentage of the undigested negative control was fit by non-linear regression using a custom MATLAB script to derive protein digestion half-lives.

BioLayer Interferometry (BLI) kD Titrations.

Titrations were performed on an OctetRed96®: BLI system (ForteBio, Menlo Park, Calif.) using streptavidin-coated probe tips. Tips were equilibrated for 10 m in 50× kinetics buffer, designed to reduce nonspecific binding (PBS, pH 7.4, 0.5% w/v BSA, 0.05% v/v Tween 20) and loaded with 25-40 nM biotinylated HA of one of six subtypes in 50× kinetics buffer for 15 m. Following a 10 m wash and 10 m baseline reading in the 50× kinetics buffer, association rates were measured by incubating each tip for 30 m in different concentrations of purified HB36.5 or HB36.6 protein spanning the predicted $k_d$ for the given HA subtype, diluted in 50× kinetics buffer. Dissociation was measured by then incubating the tips in 50× kinetics buffer for a further 30 m. HB36.6 did not show well-defined off-rates, so equilibrium binding constants were computed from the maximum steady-state response reached during the association phase. Nonlinear regression curve fitting was done with a custom MATLAB script.

In Vitro Antiviral Neutralization.

MDCK (Madin Darby canine kidney), obtained from the American Type Culture Collection (ATCC, Manassas, Va.) were grown in Growth medium comprising minimum essential medium (MEM) with non-essential amino acids, 5% FBS and 0.22% NaHCO3. Influenza A/California/07/2009 (H1N1), A/Puerto Rico/08/1934 (H1N1), A/New Caledonia/20/1999 (H1N1), A/Hong Kong/213/2003 (H5N1), and A/Duck/MN/1525/1981 (H5N1) were obtained from the Center for Disease Control (Atlanta, Ga.). The viruses were prepared in Madin Darby canine kidney (MDCK) cells, placed in ampules and frozen at −80° C. Cells are seeded to 96-well flat-bottomed tissue culture plates at the proper cell concentration to establish confluent cell monolayers and incubated overnight at 37° C. Various dilutions of test compound are added to each well. Ribavirin (1- -D-ribo-furanosyl-1,2,4-triazole-3-carboxamide), and HB36.6 were tested in half-log increments from 320 µg/ml and below. Virus is added to test compound wells and to virus control wells at about 50-100 cell culture infectious dose per ml. The virus titer is determined by a prior titration, where the most diluted virus stock is used that causes 100% CPE in all wells at the particular virus dilution. Test medium without virus is added to all toxicity control wells and to cell control wells. The plates were incubated at 37° C. for 72 hours. Sterile neutral red (0.034% in saline solution) is then added to each well. After two hours at 37° C. all medium is removed and the cells are washed with PBS and inverted to drain. Neutral red is extracted from the cells by adding an equal volume mixture of absolute ethanol and Sorensen's citrate buffer, pH 4.2. The contents of each well are mixed gently and the optical density (O.D.) values of each well are obtained by reading the plates at 540 nm with a microplate reader.

Negative-Stain Sample Preparation and Imaging.

Complexes of HA and HB36.6 were prepared for electron microscopy studies by diluting to 2.1 µg/ml in Tris buffered saline and applied to freshly glow discharged carbon coated 400 mesh copper grids for 20 seconds. Two rounds of a 3 µl droplet of 2% uranyl formate were applied and immediately blotted followed by a third 3 µl droplet blotted after 1 minute. Grids were viewed using the FEI Tecnai T12 electron microscope operating at 120 kV accelerating voltage at 52,000× magnification resulting in a pixel size 2.05 Å at the specimen level. Images were acquired on a Tietz 4 k×4 k CMOS camera using Leginon®[30,31] MSI-raster 3.0 software package at a defocus of ~1.0 µm. Microscope magnifications were calibrated using a catalase crystal prior to data collection.

EM Data Processing and 3D Volume Reconstruction.

Particles were picked automatically using DoG® Picker[32] and boxed into 96×96 pixel boxes and aligned using Xmipp CL2D clustering alignment[33]. Ten ab initio models of each complex were created using EMAN2CL[34] with C3 symmetry and based on 17 2D class averages of PR8 in complex with HB36.6. Initial models of complexes were then refined against 10,005 raw particles using EMAN[35]. The resolution of the final model was determined to be ~22 Angstroms using an FSC cut-off of 0.5. The UCSF Chimera "Fit in Map" function was used to dock structural models into the EM maps.

HB36.6 Administration and Influenza Challenge.

All animal experiments used in this study were approved by the University of Washington Institutional Animal Care and Use Committee. Groups of 6-8 week-old female BALB/c mice were anesthetized and intranasally administered protein binder (HB36.6) at concentrations varying from 0.01 to 6.0 mg/kg. Two to forty-eight hours later, the mice were anesthetized by isoflurane and challenged intranasally with 10 $MLD_{50}$ (fifty percent mouse lethal dose) of either A/California/07/09 (H1N1) (CA09) or A/PR/8/34 (H1N1) (PR8). In a therapeutic setting, mice received the protein binder 0 (2 hours post-infection), 1, 2, 3, or 4 days post infection. The mice were monitored daily for weight loss and survival until 14 days post-infection. Animals that lost more than 30% of their initial body weight were euthanized in accordance with our animal protocol. The SCID (NOD SCID gamma, strain NOD.Cg-Prkdcscid Il2rgtm1Wjl/SzJ) mice and the MyD88−/−(strain B6.129P2 (SJL)-Myd88tm1.1Defr/J) mice were purchased from Jackson Laboratory.

Nasal and Lung Viral Titers.

Nasal wash samples were collected by making an incision in the trachea and washing the nasal passages with 0.2 ml PBS (pH 7.2). Supernatants from lung homogenates were collected by mincing whole lungs in 500 µl MEM media, freeze thawing twice on dry ice, and then centrifuging at 13,000 rpm for 10 m. The viral titers in the nasal washes and supernatants from lung homogenates were determined using the $TCID_{50}$, as described previously[36]. In brief, monolayers of MDCK cells were inoculated with tenfold serial dilutions of mouse nasal washes in quadruplicate (three total replicates per sample). One hour after inoculation, the supernatants were removed and replaced with MEM media plus antibiotics and 1 µg/ml TPCK-trypsin (Sigma, St. Louis, Mo.). The viral cytopathic effect was observed for 3 days before viral infectivity in MDCK cells was measured using a hemagglutination assay with 0.33% turkey erythrocytes. The tissue viral titers were calculated using the Reed and Muench method and expressed as $\log_{10} TCID_{50}/g$ of tissue.

Enzyme-Linked Immunosorbent Assay (ELISA).

HB36.6 and CA09-specific IgG antibody levels in mouse serum were assessed by ELISA. Maxisorp® (Thermo Scientific-Nunc) were coated with either 100 ng/well of recombinant A/California/04/2009 (BEI resources), FLAG or FLAG-tagged HB36.6 in PBS overnight at 4° C. Plates were blocked with 5% nonfat milk powder in PBS for 1 h at room temperature, and then washed three times with wash buffer (PBS-T; phosphate-buffered saline containing 0.05% Tween 20). Two-fold serial dilutions of samples were added to the wells and plates were incubated for 1 hr at room temperature. Following three washes with PBS-T, plates were incubated with horseradish-peroxidase conjugated goat anti-mouse IgG (1/3,000 dilution) secondary antibodies (Thermo Scientific Pierce) for 1 h at room temperature. After five washes with PBS-T, TMB substrate (KPL) was added to the wells for 30 min at room temperature. Color development was stopped by the addition of TMB Stop solution (KPL), and the plates were read at 450 nm to measure relative optical densities (O.D.) HB36.6 specific antibody levels were determined as the difference between the O.D. measured against FLAG-tagged HB36.6 minus the O.D. measured against FLAG-only.

Bio-Plex Analysis of Cytokine Production in Lung Homogenates.

The concentrations of cytokines in lung tissue were measured. On days 2 and 4 post-infection, 8 mice per group were sacrificed and whole lung tissue was collected and immediately frozen. Lungs were thawed, weighed and lysed using the Bio-Plex® Cell Lysis Kit (Bio-Rad, Hercules, Calif.). The levels of interleukin (IL)-6, IL-10. IL-12(p70), interferon (IFN)-γ, and tumor necrosis factor (TNF)-α in the lysate were measured using a Bio-Plex) multiplex bead array kit (Bio-Rad, Hercules, Calif.). The Bio-Plex® assay was performed in accordance with the manufacturer's instructions.

Histology and Immunohistochemistry.

During in vivo challenge experiments, lungs were removed from mice and immersed in 10% neutral buffered formalin. Following fixation, tissues were removed from formalin and placed in paraffin. Immunohistochemical staining was performed on the Leica Bond Automated Immunostainer. Sections were deparaffinized in Leica Bond Dewax Solution (Leica Cat No. AR922) and rehydrated through 100% EtOH. After antigen retrieval with EDTA buffer pH 9.0 (Lieca Bond Epitope Retrieval Solution 2, Cat No AR9640) at 100° C. for 20 minutes and blocking endogenous peroxidase activity with 3.0% $H_2O_2$ for 5 minutes and blocking with 10% Normal Donkey Serum in TBS for 20 minutes the sections were incubated with Goat anti Influenza A Virus, (Meridian Life Science Inc. Cat No. B65141G) at 1:2000 or Normal Goat IgG, isotype control. (Invitrogen Cat No. 02-6202) at (1:5000 dilution) both in Bond Primary Antibody Diluent (Leica Cat No. AR9352) for 30 minutes at room temperature. Sections were then incubated with Rabbit anti Goat IgG (Jackson ImmunoResearch Cat. No. 305-005-045) 1:1500+5% Normal Donkey Serum for 8 minutes at RT followed by incubation with Goat anti Rabbit Poly-HRP polymer secondary detection (Leica Cat No DS9800) for 8 minutes at room temperature. Sections were then incubated with Leica Bond Mixed Refine DAB substrate detection for 10 minutes at room temperature. (Leica Cat No DS9800). After washing with $DIH_2O$ the sections were counter stained with Hematoxylin solution (Leica Bond Refine Kit) dehydrated through 100% EtOH, cleared in Xylene and mounted with synthetic resin mounting medium and 1.5 coverslip.

Statistical Analyses.

All of the analyses were performed using Graphpad® Prism version 5.01. A Student's t test (to compare two samples) and analysis of variance (ANOVA) (to compare multiple samples) were used for statistical analysis. Survival analysis was performed by using the Kaplan-Meier log-rank test. A P value of <0.05 was considered to be significant.

REFERENCES

1. DiLillo, D. J., Tan, G. S., Palese, P. & Ravetch, J. V. Broadly neutralizing hemagglutinin stalk-specific antibodies require FcgammaR interactions for protection against influenza virus in vivo. in *Nature medicine*. Vol. 20 143-151 (2014).
2. Webster, R. G., Bean, W. J., Gorman, O. T., Chambers, T. M. & Kawaoka, Y. Evolution and ecology of influenza A viruses. in *Microbiological reviews*, Vol. 56 152-179 (1992).
3. Falcone, V. et al. Influenza virus A(H1N1)pdm09 hemagglutinin polymorphism and associated disease in southern Germany during the 2010/11 influenza season. in *Archives of virology*, Vol. 158 1297-1303 (2013).
4. Lambert, L. C. & Fauci, A. S. Influenza vaccines for the future. in *N. Engl. J. Med.*, Vol. 363 2036-2044 (2010).
5. Girard, M. P., Tam, J. S., Assossou, O. M. & Kieny, M. P. The 2009 A (H1N1) influenza virus pandemic: A review. in *Vaccine*, Vol. 28 4895-4902 (2010).
6. Corti, D. et al. A Neutralizing Antibody Selected from Plasma Cells That Binds to Group 1 and Group 2 Influenza A Hemagglutinins. in *Science*, Vol. 333 850-856 (2011).
7. Ekiert, D. C. & Wilson. I. A. Broadly neutralizing antibodies against influenza virus and prospects for universal therapies. in *Current opinion in virology*, Vol. 2 134-141 (2012).
8. Krammer, F. & Palese, P. Influenza virus hemagglutinin stalk-based antibodies and vaccines, in *Current opinion in virology*, Vol. 3 521-530 (Elsevier B. V., 2013).
9. Bournazos, S., et al. Broadly neutralizing anti-HIV-1 antibodies require Fc effector functions for in vivo activity. *Cell* 158, 1243-1253 (2014).
10. Tharakaraman, K., Subramanian, V. Cain, D., Sasisekharan, V. & Sasisekharan, R. Broadly neutralizing influenza hemagglutinin stem-specific antibody CR8020 targets residues that are prone to escape due to host selection pressure. *Cell host & microbe* 15, 644-651 (2014).
11. Fleishman, S. J. et al. Computational Design of Proteins Targeting the Conserved Stem Region of Influenza Hemagglutinin. in *Science*, Vol. 332 816-821 (2011).
12. Whitehead, T. A., et al. Optimization of affinity, specificity and function of designed influenza inhibitors using deep sequencing. in *Nature biotechnology*, Vol. 30 543-548 (Nature Publishing Group, 2012).
13. De Clercq, E. Antiviral agents active against influenza A viruses. *Nature reviews. Drug discovery* 5, 1015-1025 (2006).
14. McCullers, J. A. The co-pathogenesis of influenza viruses with bacteria in the lung. in *Nat Rev Micro*, Vol. 12 252-262 (2014).
15. Shrestha, S. et al. Identifying the Interaction Between Influenza and Pneumococcal Pneumonia Using Incidence Data. in *Science translational medicine*, Vol. 5 191ra184-191ra184 (2013).
16. Connaris, H. et al. Prevention of influenza by targeting host receptors using engineered proteins. in *P Natl Acad Sci Usa*, Vol. 111 6401-6406 (2014).
17. Ohbo, K. et al. Modulation of hematopoiesis in mice with a truncated mutant of the interleukin-2 receptor gamma chain. *Blood* 87, 956-967 (1996).
18. Ishikawa, F., et al. Development of functional human blood and immune systems in NOD/SCID/IL2 receptor {gamma} chain(null) mice. *Blood* 106, 1565-1573 (2005).
19. Sco, S. U. et al. MyD88 signaling is indispensable for primary influenza A virus infection but dispensable for secondary infection. *Journal of virology* 84, 12713-12722 (2010).
20. Koyama, S., et al. Differential role of TLR- and RLR-signaling in the immune responses to influenza A virus infection and vaccination. *Journal of immunology* 179, 4711-4720 (2007).
21. Ichinohe, T., Lee. H. K., Ogura, Y., Flavell, R. & Iwasaki, A. Inflammasome recognition of influenza virus is essential for adaptive immune responses. *The Journal of experimental medicine* 206, 79-87 (2009).
22. Morbidity and Mortality Weekly Report. 1-36 (2010).
23. Kunkel, T. A. Rapid and efficient site-specific mutagenesis without phenotypic selection. in *P Natl Acad Sci Usa*, Vol. 82 488-492 (1985).
24. Chao, G. et al. Isolating and engineering human antibodies using yeast surface display. in *Nature protocols*, Vol. 1 755-768 (2006).
25. Araya, C. L. et al. A fundamental protein property, thermodynamic stability, revealed solely from large-scale measurements of protein function. *Proceedings of the National Academy of Sciences of the United States of America* 109, 16858-16863 (2012).
26. Patrick, W. M., Firth, A. E. & Blackburn, J. M. User-friendly algorithms for estimating completeness and diversity in randomized protein-encoding libraries. *Protein engineering* 16, 451-457 (2003).

27. Hoover, D. M. & Lubkowski, J. DNAWorks: an automated method for designing oligonucleotides for PCR-based gene synthesis. *Nucleic acids research* 30. e43 (2002).
28. Gibson, D. G. et al. Enzymatic assembly of DNA molecules up to several hundred kilobases. *Nature methods* 6, 343-345 (2009).
29. Studier, F. W. Protein production by auto-induction in high density shaking cultures. *Protein expression and purification* 41, 207-234 (2005).
30. Suloway, C., et al. *Automated molecular microscopy: the new Leginon system. Journal of structural biology* 151, 41-60 (2005).
31. Lander, G. C., et al. Appion: an integrated, database-driven pipeline to facilitate EM image processing. *Journal of structural biology* 166, 95-102 (2009).
32. Voss, N. R., Yoshioka, C. K., Radermacher, M., Potter, C. S. & Carragher, B. DoG Picker and TiltPicker: software tools to facilitate particle selection in single particle electron microscopy. *Journal of structural biology* 166, 205-213 (2009).
33. Sorzano, C. O. et al. A clustering approach to multireference alignment of single-particle projections in electron microscopy. *Journal of structural biology* 171, 197-206 (2010).
34. Tang, G. et al. EMAN2: an extensible image processing suite for electron microscopy. *Journal of structural biology* 157, 38-46 (2007).
35. Ludtke, S. J., Baldwin, P. R. & Chiu, W. EMAN: semiautomated software for high-resolution single-particle reconstructions. *Journal of structural biology* 128, 82-97 (1999).
36. Szretter, K. J., Balish, A. L. & Katz, J. M. Influenza: propagation, quantification, and storage. *Current protocols in microbiology* Chapter 15, Unit 15G 11 (2006).

Example 2

Background:

The ferret is the preclinical standard for evaluating candidate influenza vaccines for clinical testing. Ferrets are susceptible to the same influenza viruses as humans and exhibit similar pathology. Generally, therapies that effectively protect a ferret will translate to protection in humans. HB36.6, is designed to bind to the fusion region of the influenza hemagglutinin, neutralizes influenza in vitro, and protects mice from lethal challenge as shown herein.

Objective:

The purpose of this experiment is to determine an appropriate dose of HB36.6 that results in protection against lethal challenge with influenza.

Methods:

1. At the beginning of the study, ferrets were anesthetized using isoflurane and a temperature transponder was placed in the inguinal region of each ferret. This allowed for daily temperature readings.
2. The next day, ferrets were anesthetized using isoflurane and then intranasally injected with protein binder, dose range 2.5 mg protein per kg body weight ferret, or 10 mg/kg (0.5 ml, each nostril). The Naïve controls received PBS (0.5 ml, each nostril).
3. At 2 hours post-binder administration, ferrets were placed in an aerosol chamber and challenged with A/California/07/2009 (CA09) influenza virus.
4. After infection, the ferrets were monitored daily for weight loss, temperature, and clinical signs of disease.
5. Blood and nasal swabs were collected on Days 1, 2, and 3 post-challenge to determine viral loads in infected ferrets.
6. Ferrets were sacrificed on day 3 post-challenge and trachea, lung, and nasal turbinates were collected to analyze viral loads and gross histology.

The results of this study are summarized in FIG. 6, which shows that intranasal delivery of HB36.6 affords prophylactic protection against lethal Influenza virus challenge in ferrets. This data demonstrates that HB36.6 provides a prophylactic benefit in treating and ameliorating influenza disease in the ferret pre-clinical model for influenza.

We claim:

1. An isolated polypeptide comprising the amino acid sequence of SEQ ID NO:1, wherein the polypeptide does not comprise the amino acid sequence of 1u84 (SEQ ID NO: 5).

2. The isolated polypeptide of claim 1, comprising the amino acid sequence of SEQ ID NO:2.

3. The isolated polypeptide of claim 1, wherein residue 46 is selected from the group consisting of R, Y, C, and W.

4. The isolated polypeptide of claim 1, wherein residue 46 is R.

5. The isolated polypeptide of claim 1, wherein residue 46 is R and one or more of the following is true:
 (a) residue 16 is N;
 (b) residue 31 is T;
 (c) residue 33 is Q;
 (d) residue 70 is R; and
 (e) residue 71 is T.

6. The isolated polypeptide of claim 1, wherein one or more of the following is true:
 (a) residue 45 is N;
 (b) residue 65 is R; and
 (c) residue 66 is L.

7. The isolated polypeptide of claim 1, comprising a polypeptide at least 90% identical to the amino acid sequence of SEQ ID NO:3 or SEQ ID NO:4.

8. The isolated polypeptide of claim 1, wherein one or more of the following are true:
 (a) residue 33 is A, C, T, or S;
 (b) residue 46 is H;

(c) residue 59 is F, W, or Y; and
(d) residue 63 is P.

9. The isolated polypeptide of claim 1, wherein one or more of the following are true:
(a) residue 33 is C, S, A, T, or V;
(b) residue 53 is a small smaller polar/charged residue;
(c) residue 55 is S, T, or A;
(d) residue 59 is L, P, or Y;
(e) residue 68 is L;
(f) residue 72 is W; and
(g) residue 73 is E.

10. The isolated polypeptide of claim 1, wherein one or more of the following are true:
(a) residue 36 is K;
(b) residue 52 is L;
(c) residue 53 is a small polar or charged AA; and
(d) residue 59 is Y or F.

11. The isolated polypeptide of claim 1, wherein one or more of the following are true:
(a) residue 33 is P;
(b) residue 69 is Y;
(c) residue 70 is a polar or charged AA; and
(d) residue 73 is E.

12. The isolated polypeptide of claim 1, wherein one or more of the following are true:
(a) residue 31 is any amino acid other than a charged amino acid;
(b) residue 33 is S or T;
(c) residue 52 is L;
(d) residue 53 is a small polar or charged AA and is not R;
(e) residue 59 is V;
(f) residue 69 is a negative AA;
(g) residue 70 is any non-positively charged AA;
(h) residue 72 is a negative AA;
(i) residue 73 is a negative AA; and
(j) residue 76 is any amino acid other than R, such as a negative AA.

13. The isolated polypeptide of claim 1, wherein one or more of the following are true:
(a) residue 46 is H;
(b) residue 53 is a small polar or charged AA;
(c) residue 63 is R; and
(d) residue 76 is a negative AA.

14. The isolated polypeptide of claim 8, wherein all of the listed residue options are true.

15. The isolated polypeptide according to claim 1, wherein the polypeptide comprises a tag.

16. An isolated nucleic acid encoding the polypeptide of claim 1.

17. A recombinant expression vector comprising the nucleic acid of claim 16, operatively linked to a suitable control sequence.

18. A recombinant host cell comprising the recombinant expression vector of claim 17.

19. A pharmaceutical composition, comprising one or more polypeptides according to claim 1 and a pharmaceutically acceptable carrier.

20. A method for treating and/or limiting an influenza infection, comprising administering to a subject in need thereof a therapeutically effective amount of one or more polypeptides of claim 1, salts thereof, conjugates thereof, or pharmaceutical compositions thereof, to treat and/or limit the influenza infection.

21. The method of claim 20, wherein the therapeutically effective amount of one or more polypeptides, salts thereof, conjugates thereof, or pharmaceutical compositions thereof are administered mucosally.

22. The method of claim 21, wherein the mucosal administration comprises intranasal administration.

23. The method of claim 20, wherein the therapeutically effective amount of one or more polypeptides, salts thereof, conjugates thereof, or pharmaceutical compositions thereof are administered orally.

24. The method of claim 20, wherein the subject is immune-compromised and/or is 65 years of age or older.

25. A method for diagnosing an influenza infection, or monitoring progression of an influenza infection, comprising
(a) contacting a biological sample from a subject suspected of having an influenza infection with a diagnostically effective amount of one or more polypeptides of claim 1, under conditions suitable for binding of the polypeptide to a viral HA protein present in the sample; and
(b) detecting polypeptide-viral HA binding complexes, where the presence of such binding complexes indicates that the subject has an influenza infection, or provides a measure progression of an influenza infection.

26. A method for identifying candidate influenza vaccines, comprising
contacting test compounds with one or more polypeptides of claim 1 under conditions suitable for polypeptide binding;
removing unbound test compounds; and
identifying those test compounds that bind to the polypeptide of the invention, wherein such test compounds are candidate influenza vaccines.

27. A method for identifying candidate compounds for treating, limiting, and/or diagnosing influenza infection, comprising
contacting an influenza HA protein with (i) test compounds and (ii) a polypeptide of claim 1, under conditions suitable for binding of the HA protein to the polypeptide of the present invention; and
identifying those test compounds that outcompete the polypeptide for binding to the HA protein, wherein such test compounds are candidate compounds for treating, limiting, and/or diagnosing influenza infection.

* * * * *

SEQUENCE LISTING

```
<160> NUMBER OF SEQ ID NOS: 6

<210> SEQ ID NO 1
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: X is optional, if present can be any amino acid
<220> FEATURE:
<221> NAME/KEY: MISC_FEATURE
<222> LOCATION: (6)..(6)
<223> OTHER INFORMATION: X is any amino acid
<220> FEATURE:
<221> NAME/KEY: MISC_FEATURE
<222> LOCATION: (7)..(7)
<223> OTHER INFORMATION: X is K, R or Q
<220> FEATURE:
<221> NAME/KEY: MISC_FEATURE
<222> LOCATION: (8)..(8)
<223> OTHER INFORMATION: X is S or Q
```

-continued

```
<220> FEATURE:
<221> NAME/KEY: MISC_FEATURE
<222> LOCATION: (9)..(9)
<223> OTHER INFORMATION: X is L, K, F, D or V
<220> FEATURE:
<221> NAME/KEY: MISC_FEATURE
<222> LOCATION: (10)..(10)
<223> OTHER INFORMATION: X is N, Q, D, or E
<220> FEATURE:
<221> NAME/KEY: MISC_FEATURE
<222> LOCATION: (11)..(11)
<223> OTHER INFORMATION: X is K, Q, R or polar or charged amino acid
<220> FEATURE:
<221> NAME/KEY: MISC_FEATURE
<222> LOCATION: (12)..(12)
<223> OTHER INFORMATION: X is L, Q, K, T, or R
<220> FEATURE:
<221> NAME/KEY: MISC_FEATURE
<222> LOCATION: (13)..(13)
<223> OTHER INFORMATION: X is L, M, or I
<220> FEATURE:
<221> NAME/KEY: MISC_FEATURE
<222> LOCATION: (14)..(14)
<223> OTHER INFORMATION: X is L or polar
<220> FEATURE:
<221> NAME/KEY: MISC_FEATURE
<222> LOCATION: (15)..(15)
<223> OTHER INFORMATION: X is D or E
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (17)..(17)
<223> OTHER INFORMATION: X is V or I
<220> FEATURE:
<221> NAME/KEY: MISC_FEATURE
<222> LOCATION: (18)..(18)
<223> OTHER INFORMATION: X is G or any polar amino acid
<220> FEATURE:
<221> NAME/KEY: MISC_FEATURE
<222> LOCATION: (21)..(21)
<223> OTHER INFORMATION: X is D or A
<220> FEATURE:
<221> NAME/KEY: MISC_FEATURE
<222> LOCATION: (23)..(23)
<223> OTHER INFORMATION: X is F or L
<220> FEATURE:
<221> NAME/KEY: MISC_FEATURE
<222> LOCATION: (27)..(27)
<223> OTHER INFORMATION: X is K or P
<220> FEATURE:
<221> NAME/KEY: MISC_FEATURE
<222> LOCATION: (28)..(28)
<223> OTHER INFORMATION: X is D, N, G, H or R
<220> FEATURE:
<221> NAME/KEY: MISC_FEATURE
<222> LOCATION: (31)..(31)
<223> OTHER INFORMATION: X is D, T, A, N, or any charged or polar amino
      acid
<220> FEATURE:
<221> NAME/KEY: MISC_FEATURE
<222> LOCATION: (32)..(32)
<223> OTHER INFORMATION: X is Y or R, or any other polar amino acid
<220> FEATURE:
<221> NAME/KEY: MISC_FEATURE
<222> LOCATION: (33)..(33)
<223> OTHER INFORMATION: X is E, Q, S, T, A, C, or P
<220> FEATURE:
<221> NAME/KEY: MISC_FEATURE
<222> LOCATION: (35)..(35)
<223> OTHER INFORMATION: X is E, R or A
<220> FEATURE:
<221> NAME/KEY: MISC_FEATURE
<222> LOCATION: (38)..(38)
<223> OTHER INFORMATION: X is L or V
```

-continued

```
<220> FEATURE:
<221> NAME/KEY: MISC_FEATURE
<222> LOCATION: (45)..(45)
<223> OTHER INFORMATION: X is E, N, S, T, H, or Q
<220> FEATURE:
<221> NAME/KEY: MISC_FEATURE
<222> LOCATION: (46)..(46)
<223> OTHER INFORMATION: X is S, T, R or H
<220> FEATURE:
<221> NAME/KEY: MISC_FEATURE
<222> LOCATION: (51)..(51)
<223> OTHER INFORMATION: X is A or V
<220> FEATURE:
<221> NAME/KEY: MISC_FEATURE
<222> LOCATION: (53)..(53)
<223> OTHER INFORMATION: X is R, K, D, E, N, Q, S, or T
<220> FEATURE:
<221> NAME/KEY: MISC_FEATURE
<222> LOCATION: (54)..(54)
<223> OTHER INFORMATION: X is I, M or V
<220> FEATURE:
<221> NAME/KEY: MISC_FEATURE
<222> LOCATION: (58)..(58)
<223> OTHER INFORMATION: X is Y or F
<220> FEATURE:
<221> NAME/KEY: MISC_FEATURE
<222> LOCATION: (59)..(59)
<223> OTHER INFORMATION: X is N, Y or F
<220> FEATURE:
<221> NAME/KEY: MISC_FEATURE
<222> LOCATION: (61)..(61)
<223> OTHER INFORMATION: X is S or A
<220> FEATURE:
<221> NAME/KEY: MISC_FEATURE
<222> LOCATION: (63)..(63)
<223> OTHER INFORMATION: X is K or R
<220> FEATURE:
<221> NAME/KEY: MISC_FEATURE
<222> LOCATION: (64)..(64)
<223> OTHER INFORMATION: X is G, K or R
<220> FEATURE:
<221> NAME/KEY: MISC_FEATURE
<222> LOCATION: (65)..(65)
<223> OTHER INFORMATION: X is R, Q or A
<220> FEATURE:
<221> NAME/KEY: MISC_FEATURE
<222> LOCATION: (67)..(67)
<223> OTHER INFORMATION: X is P, V, N, I, K, R, or Q
<220> FEATURE:
<221> NAME/KEY: MISC_FEATURE
<222> LOCATION: (69)..(69)
<223> OTHER INFORMATION: X is Y or A
<220> FEATURE:
<221> NAME/KEY: MISC_FEATURE
<222> LOCATION: (70)..(70)
<223> OTHER INFORMATION: X is H, R or any charged or polar amino acids
<220> FEATURE:
<221> NAME/KEY: MISC_FEATURE
<222> LOCATION: (71)..(71)
<223> OTHER INFORMATION: X is any amino acid
<220> FEATURE:
<221> NAME/KEY: MISC_FEATURE
<222> LOCATION: (72)..(72)
<223> OTHER INFORMATION: X is Q or any charged or polar neutral amino
      acids
<220> FEATURE:
<221> NAME/KEY: MISC_FEATURE
<222> LOCATION: (73)..(73)
<223> OTHER INFORMATION: X is K, D, E, or any polar amino acid
<220> FEATURE:
<221> NAME/KEY: MISC_FEATURE
<222> LOCATION: (74)..(74)
<223> OTHER INFORMATION: X is L, F, or A
<220> FEATURE:
<221> NAME/KEY: MISC_FEATURE
<222> LOCATION: (76)..(76)
<223> OTHER INFORMATION: X is R, S, T, E, or G
```

<220> FEATURE:
<221> NAME/KEY: MISC_FEATURE
<222> LOCATION: (77)..(77)
<223> OTHER INFORMATION: X is R, Q, K, or E
<220> FEATURE:
<221> NAME/KEY: MISC_FEATURE
<222> LOCATION: (80)..(80)
<223> OTHER INFORMATION: X is E or D
<220> FEATURE:
<221> NAME/KEY: MISC_FEATURE
<222> LOCATION: (81)..(81)
<223> OTHER INFORMATION: X is L or M
<220> FEATURE:
<221> NAME/KEY: MISC_FEATURE
<222> LOCATION: (83)..(83)
<223> OTHER INFORMATION: X is Q, H or R
<220> FEATURE:
<221> NAME/KEY: MISC_FEATURE
<222> LOCATION: (85)..(85)
<223> OTHER INFORMATION: X is A, H or any polar amino acid
<220> FEATURE:
<221> NAME/KEY: MISC_FEATURE
<222> LOCATION: (86)..(90)
<223> OTHER INFORMATION: X is optional, if present can be any amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Ala Trp Xaa Pro Xaa Gly Leu Gly Xaa Xaa Ala Tyr Xaa Xaa
            20                  25                  30

Xaa Ala Xaa Glu Val Xaa Lys Ala Val Tyr Glu Thr Xaa Xaa Ala Phe
        35                  40                  45

Asp Leu Xaa Met Xaa Xaa His Trp Ile Xaa Xaa Phe Xaa Phe Xaa Xaa
        50                  55                  60

Xaa Ile Xaa Phe Xaa Xaa Xaa Xaa Xaa Ala Xaa Xaa Leu Leu Xaa
65                  70                  75                  80

Xaa Lys Xaa Ala Xaa Xaa Xaa Xaa Xaa Xaa
                85                  90

<210> SEQ ID NO 2
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: X is optional and if present it is any amino
      acid
<220> FEATURE:
<221> NAME/KEY: MISC_FEATURE
<222> LOCATION: (12)..(12)
<223> OTHER INFORMATION: X is I or any charged amino acid
<220> FEATURE:
<221> NAME/KEY: MISC_FEATURE
<222> LOCATION: (14)..(14)
<223> OTHER INFORMATION: X is any charged amino acid
<220> FEATURE:
<221> NAME/KEY: MISC_FEATURE
<222> LOCATION: (16)..(16)
<223> OTHER INFORMATION: X is any amino acid other than W or N
<220> FEATURE:
<221> NAME/KEY: MISC_FEATURE
<222> LOCATION: (21)..(21)
<223> OTHER INFORMATION: X is M, A or any charged amino acid
<220> FEATURE:
<221> NAME/KEY: MISC_FEATURE
<222> LOCATION: (23)..(23)
<223> OTHER INFORMATION: X is F or any hydrophobic amino acid -continued

```
<220> FEATURE:
<221> NAME/KEY: MISC_FEATURE
<222> LOCATION: (24)..(24)
<223> OTHER INFORMATION: X is any small amino acid  or G
<220> FEATURE:
<221> NAME/KEY: MISC_FEATURE
<222> LOCATION: (25)..(25)
<223> OTHER INFORMATION: X is L or any hydrophobic or neutral amino
      acid, but not C
<220> FEATURE:
<221> NAME/KEY: MISC_FEATURE
<222> LOCATION: (26)..(26)
<223> OTHER INFORMATION: X is any small amino acid  or G
<220> FEATURE:
<221> NAME/KEY: MISC_FEATURE
<222> LOCATION: (27)..(27)
<223> OTHER INFORMATION: X is any amino acid
<220> FEATURE:
<221> NAME/KEY: MISC_FEATURE
<222> LOCATION: (31)..(31)
<223> OTHER INFORMATION: X is D, T, or any charged amino acid
<220> FEATURE:
<221> NAME/KEY: MISC_FEATURE
<222> LOCATION: (33)..(33)
<223> OTHER INFORMATION: X is E, S, T, or Q
<220> FEATURE:
<221> NAME/KEY: MISC_FEATURE
<222> LOCATION: (34)..(35)
<223> OTHER INFORMATION: X is any small amino acid  or A
<220> FEATURE:
<221> NAME/KEY: MISC_FEATURE
<222> LOCATION: (37)..(37)
<223> OTHER INFORMATION: X is V, A, I, or L
<220> FEATURE:
<221> NAME/KEY: MISC_FEATURE
<222> LOCATION: (38)..(38)
<223> OTHER INFORMATION: X is A, I, or L
<220> FEATURE:
<221> NAME/KEY: MISC_FEATURE
<222> LOCATION: (41)..(41)
<223> OTHER INFORMATION: X is V or L
<220> FEATURE:
<221> NAME/KEY: MISC_FEATURE
<222> LOCATION: (42)..(42)
<223> OTHER INFORMATION: X is Y or any large amino acid
<220> FEATURE:
<221> NAME/KEY: MISC_FEATURE
<222> LOCATION: (43)..(43)
<223> OTHER INFORMATION: X is D, T, or S
<220> FEATURE:
<221> NAME/KEY: MISC_FEATURE
<222> LOCATION: (45)..(45)
<223> OTHER INFORMATION: X is E or N
<220> FEATURE:
<221> NAME/KEY: MISC_FEATURE
<222> LOCATION: (46)..(46)
<223> OTHER INFORMATION: X is S, R, or any polar or aromatic amino acid
<220> FEATURE:
<221> NAME/KEY: MISC_FEATURE
<222> LOCATION: (47)..(47)
<223> OTHER INFORMATION: X is A, S, or T
<220> FEATURE:
<221> NAME/KEY: MISC_FEATURE
<222> LOCATION: (49)..(49)
<223> OTHER INFORMATION: X is D or N
<220> FEATURE:
<221> NAME/KEY: MISC_FEATURE
<222> LOCATION: (51)..(51)
<223> OTHER INFORMATION: X is A or V
<220> FEATURE:
<221> NAME/KEY: MISC_FEATURE
<222> LOCATION: (52)..(52)
<223> OTHER INFORMATION: X is M, V, or L
<220> FEATURE:
<221> NAME/KEY: MISC_FEATURE
<222> LOCATION: (54)..(54)
<223> OTHER INFORMATION: X is I, M, or V
```

```
<220> FEATURE:
<221> NAME/KEY: MISC_FEATURE
<222> LOCATION: (58)..(58)
<223> OTHER INFORMATION: X is Y or a hydrophobic amino acid
<220> FEATURE:
<221> NAME/KEY: MISC_FEATURE
<222> LOCATION: (59)..(59)
<223> OTHER INFORMATION: X is F or Y
<220> FEATURE:
<221> NAME/KEY: MISC_FEATURE
<222> LOCATION: (60)..(60)
<223> OTHER INFORMATION: X is F or T
<220> FEATURE:
<221> NAME/KEY: MISC_FEATURE
<222> LOCATION: (61)..(61)
<223> OTHER INFORMATION: X is A or G
<220> FEATURE:
<221> NAME/KEY: MISC_FEATURE
<222> LOCATION: (63)..(63)
<223> OTHER INFORMATION: X is K, R, or P
<220> FEATURE:
<221> NAME/KEY: MISC_FEATURE
<222> LOCATION: (64)..(64)
<223> OTHER INFORMATION: X is R or G
<220> FEATURE:
<221> NAME/KEY: MISC_FEATURE
<222> LOCATION: (65)..(65)
<223> OTHER INFORMATION: X is R or A
<220> FEATURE:
<221> NAME/KEY: MISC_FEATURE
<222> LOCATION: (66)..(66)
<223> OTHER INFORMATION: X is any amino acid
<220> FEATURE:
<221> NAME/KEY: MISC_FEATURE
<222> LOCATION: (67)..(67)
<223> OTHER INFORMATION: X is V, L, I, R, Q, or N
<220> FEATURE:
<221> NAME/KEY: MISC_FEATURE
<222> LOCATION: (69)..(69)
<223> OTHER INFORMATION: X is A or any hydrophobic or charged or polar
      amino acid
<220> FEATURE:
<221> NAME/KEY: MISC_FEATURE
<222> LOCATION: (70)..(70)
<223> OTHER INFORMATION: X is H, R, or any charged amino acid
<220> FEATURE:
<221> NAME/KEY: MISC_FEATURE
<222> LOCATION: (71)..(71)
<223> OTHER INFORMATION: X is S, T, L, or K
<220> FEATURE:
<221> NAME/KEY: MISC_FEATURE
<222> LOCATION: (72)..(72)
<223> OTHER INFORMATION: X is Q, T or R
<220> FEATURE:
<221> NAME/KEY: MISC_FEATURE
<222> LOCATION: (73)..(73)
<223> OTHER INFORMATION: X is K or Q
<220> FEATURE:
<221> NAME/KEY: MISC_FEATURE
<222> LOCATION: (74)..(74)
<223> OTHER INFORMATION: X is L, A, or F
<220> FEATURE:
<221> NAME/KEY: MISC_FEATURE
<222> LOCATION: (76)..(77)
<223> OTHER INFORMATION: X is R or K
<220> FEATURE:
<221> NAME/KEY: MISC_FEATURE
<222> LOCATION: (80)..(80)
<223> OTHER INFORMATION: X is E or any charged amino acid
<220> FEATURE:
<221> NAME/KEY: MISC_FEATURE
<222> LOCATION: (83)..(83)
<223> OTHER INFORMATION: X is Q, H or K
<220> FEATURE:
<221> NAME/KEY: MISC_FEATURE
<222> LOCATION: (85)..(85)
<223> OTHER INFORMATION: X is A or H
```

```
<220> FEATURE:
<221> NAME/KEY: MISC_FEATURE
<222> LOCATION: (86)..(90)
<223> OTHER INFORMATION: X is optional and if present it is any amino
      acid

<400> SEQUENCE: 2

Xaa Xaa Xaa Xaa Xaa Gly Gln Gln Leu Asn Arg Xaa Leu Xaa Glu Xaa
1               5                   10                  15

Ile Gly Ala Trp Xaa Pro Xaa Xaa Xaa Xaa Asp Ala Tyr Xaa Tyr
            20                  25                  30

Xaa Xaa Xaa Glu Xaa Xaa Glu Ala Xaa Xaa Thr Xaa Xaa Xaa Phe
            35                  40                  45

Xaa Leu Xaa Xaa Lys Xaa His Trp Ile Xaa Xaa Xaa Phe Xaa Xaa
    50                  55                  60

Xaa Xaa Xaa Phe Xaa Xaa Xaa Xaa Xaa Ala Xaa Xaa Leu Leu Xaa
65              70                  75                  80

Leu Lys Xaa Ala Xaa Xaa Xaa Xaa Xaa
                85                  90

<210> SEQ ID NO 3
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (86)..(90)
<223> OTHER INFORMATION: optionally absent

<400> SEQUENCE: 3

Ser Asn Ala Met Asp Gly Gln Gln Leu Asn Arg Leu Leu Leu Glu Asn
1               5                   10                  15

Ile Gly Ala Trp Asp Pro Phe Gly Leu Gly Lys Asp Ala Tyr Thr Tyr
            20                  25                  30

Gln Ala Ala Glu Val Leu Lys Ala Val Tyr Glu Thr Asn Arg Ala Phe
            35                  40                  45

Asp Leu Ala Met Arg Ile His Trp Ile Tyr Asn Phe Ala Phe Lys Arg
    50                  55                  60

Arg Ile Pro Phe Ala Arg Thr Gln Lys Leu Ala Arg Arg Leu Leu Glu
65              70                  75                  80

Leu Lys Gln Ala Ala Ser Ser Pro Leu Pro
                85                  90

<210> SEQ ID NO 4
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (86)..(90)
<223> OTHER INFORMATION: optionally absent
```

```
<400> SEQUENCE: 4

Ser Asn Ala Met Asp Gly Gln Gln Leu Asn Arg Leu Leu Leu Glu Trp
1               5                   10                  15

Ile Gly Ala Trp Asp Pro Phe Gly Leu Gly Lys Asp Ala Tyr Asp Tyr
                20                  25                  30

Glu Ala Ala Glu Val Leu Lys Ala Val Tyr Glu Thr Glu Ser Ala Phe
            35                  40                  45

Asp Leu Ala Met Arg Ile His Trp Ile Tyr Asn Phe Ala Phe Lys Arg
        50                  55                  60

Gln Ile Pro Phe Ala His Ala Gln Lys Leu Ala Arg Arg Leu Leu Glu
65                  70                  75                  80

Leu Lys Gln Ala Ala Ser Ser Pro Leu Pro
                85                  90

<210> SEQ ID NO 5
<211> LENGTH: 90
<212> TYPE: PRT
<213> ORGANISM: Artificial Sequence
<220> FEATURE:
<223> OTHER INFORMATION: Synthetic

<400> SEQUENCE: 5

Ser Asn Ala Met Asp Gly Gln Gln Leu Asn Arg Leu Leu Leu Glu Trp
1               5                   10                  15

Ile Gly Ala Trp Asp Pro Phe Gly Leu Gly Lys Asp Ala Tyr Asp Val
                20                  25                  30

Glu Ala Ala Ser Val Leu Gln Ala Val Tyr Glu Thr Glu Asp Ala Arg
            35                  40                  45

Thr Leu Ala Ala Arg Ile Gln Ser Ile Tyr Glu Phe Ala Phe Asp Glu
        50                  55                  60

Pro Ile Pro Phe Pro His Cys Leu Lys Leu Ala Arg Arg Leu Leu Glu
65                  70                  75                  80

Leu Lys Gln Ala Ala Ser Cys Pro Leu Pro
                85                  90

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Asp Tyr Lys Asp Asp Asp Asp Lys
1               5
```